United States Patent
Johnson et al.

(10) Patent No.: US 8,845,675 B2
(45) Date of Patent: Sep. 30, 2014

(54) CATHETER WITH DISRUPTABLE GUIDEWIRE CHANNEL

(75) Inventors: Eric Gerard Johnson, Flagstaff, AZ (US); George N. Foutrakis, Oxford, PA (US); DH Perkins, Santa Rosa, CA (US); Sherif Eskaros, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/620,062

(22) Filed: Sep. 14, 2012

(65) Prior Publication Data

US 2013/0041316 A1     Feb. 14, 2013

Related U.S. Application Data

(60) Division of application No. 11/501,089, filed on Aug. 7, 2006, now Pat. No. 8,308,749, which is a continuation-in-part of application No. 10/346,599, filed on Jan. 17, 2003, now abandoned.

(51) Int. Cl.
*A61M 29/00* (2006.01)

(52) U.S. Cl.
USPC ........... 606/192; 606/108; 606/194; 623/1.11

(58) Field of Classification Search
USPC .......... 600/115, 466, 585; 606/108, 191, 192, 606/194, 195, 196; 623/1.11, 1.12; 604/524, 96.01, 103, 103.03, 103.05, 604/103.06, 103.07, 103.08, 103.14, 916, 604/103.04
See application file for complete search history.

(56) References Cited

U.S. PATENT DOCUMENTS

| | | |
|---|---|---|
| 4,501,580 A | 2/1985 | Glassman |
| 4,762,129 A | 8/1988 | Bonzel |
| 4,881,547 A | 11/1989 | Danforth |
| 4,917,666 A | 4/1990 | Solar et al. |
| 4,960,410 A | 10/1990 | Pinchuk |
| 4,983,167 A | 1/1991 | Sahota |
| 5,040,548 A | 8/1991 | Yock |
| 5,049,131 A | 9/1991 | Deuss |
| 5,141,494 A | 8/1992 | Danforth et al. |
| 5,160,321 A | 11/1992 | Sahota |
| 5,211,654 A | 5/1993 | Kaltenbach |
| 5,263,932 A | 11/1993 | Jang |
| 5,324,269 A | 6/1994 | Miraki |
| 5,336,184 A | 8/1994 | Teirstein |
| 5,370,617 A | 12/1994 | Sahota |
| 5,458,639 A | 10/1995 | Tsukashima et al. |
| 5,554,118 A | 9/1996 | Jang |
| 5,575,771 A | 11/1996 | Walinsky |

(Continued)

FOREIGN PATENT DOCUMENTS

EP         0400713         5/1990

*Primary Examiner* — David Eastwood
(74) *Attorney, Agent, or Firm* — Wayne D. House

(57) ABSTRACT

The present invention is a catheter device that includes a disruptable guidewire channel. The guidewire channel is configured to provide necessary trackability of the catheter along the guidewire during introduction of the catheter to a treatment site. Once treatment is completed, the guidewire channel can then be disrupted so as to free the guidewire from the catheter in situ. The apparatus of the present invention provides distinct advantages over existing over-the-wire and rapid exchange catheter introduction methods, including the ability to achieve much faster treatment implement exchanges, the ability to rapidly deliver multiple treatment implements in series, and the ability to maintain multiple treatment implements simultaneously at a treatment site using a single guidewire.

7 Claims, 28 Drawing Sheets

(56) References Cited

U.S. PATENT DOCUMENTS

| | | |
|---|---|---|
| 5,752,934 A | 5/1998 | Campbell et al. |
| 5,868,704 A | 2/1999 | Campbell et al. |
| 5,895,405 A | 4/1999 | Inderbitzen |
| 6,007,517 A | 12/1999 | Anderson |
| 6,120,477 A | 9/2000 | Campbell et al. |
| 6,217,567 B1 * | 4/2001 | Zadno-Azizi et al. ........ 604/530 |
| 6,221,042 B1 | 4/2001 | Adams |
| 6,319,244 B2 | 11/2001 | Suresh et al. |
| 6,371,961 B1 | 4/2002 | Osborne et al. |
| 6,394,995 B1 | 5/2002 | Solar et al. |
| 6,702,782 B2 | 3/2004 | Miller et al. |
| 6,709,440 B2 | 3/2004 | Callol et al. |
| 6,878,329 B2 | 4/2005 | Blankenship et al. |
| 6,942,680 B2 | 9/2005 | Grayzel et al. |
| 2001/0027310 A1 | 10/2001 | Parisi et al. |
| 2001/0031979 A1 | 10/2001 | Ricci |
| 2003/0055483 A1 | 3/2003 | Gumm |
| 2004/0172119 A1 * | 9/2004 | Eidenschink ................ 623/1.11 |
| 2005/0059957 A1 | 3/2005 | Campbell et al. |

* cited by examiner

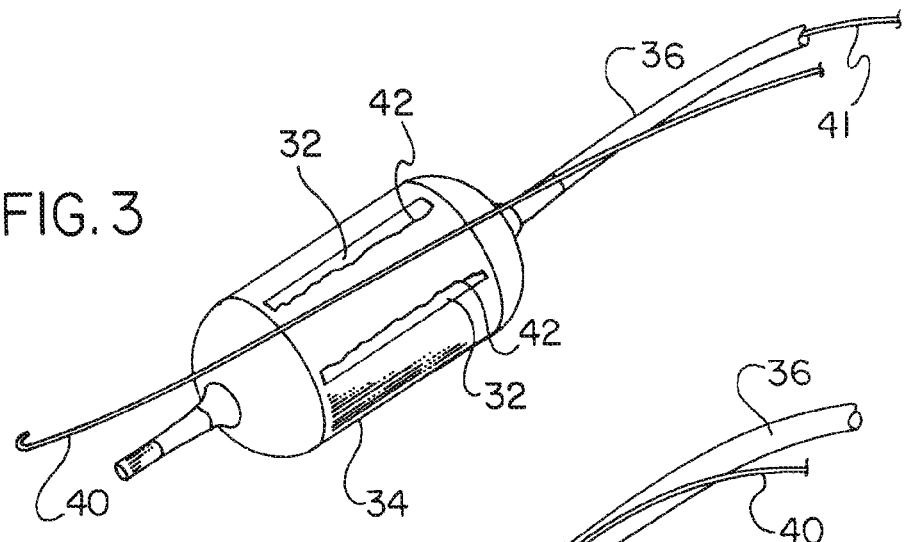
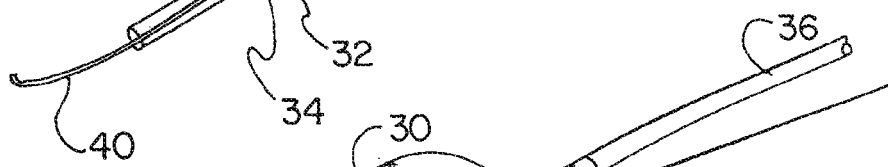
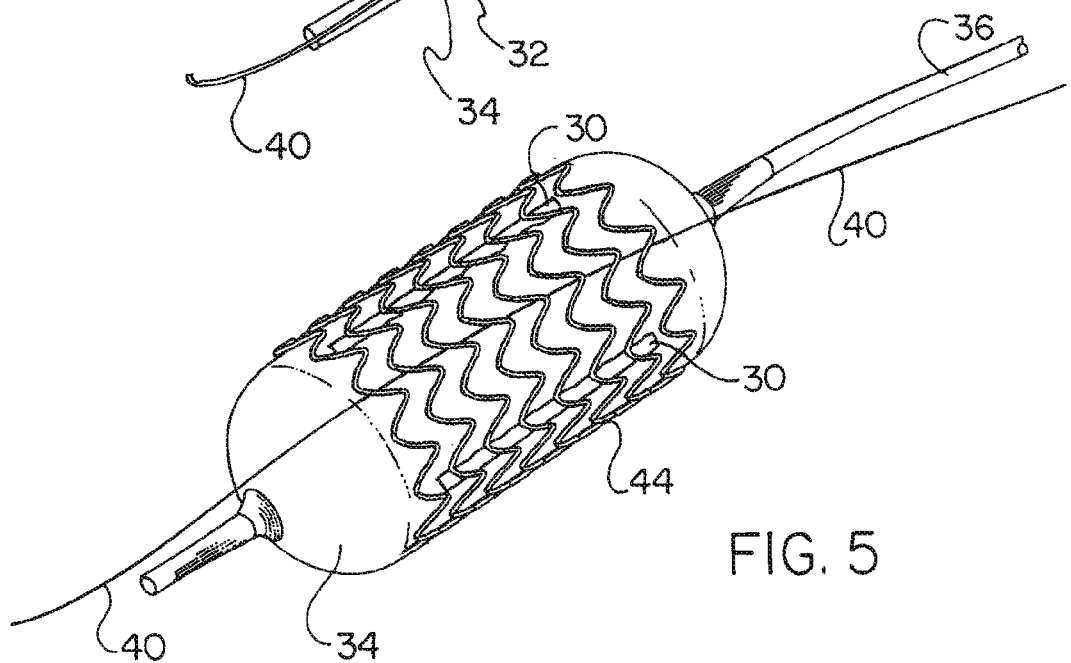

CATHETER WITH DISRUPTABLE GUIDEWIRE CHANNEL

CROSS REFERENCE TO RELATED APPLICATIONS

This application is a divisional of commonly owned and copending U.S. patent application Ser. No. 11/501,089, filed on Aug. 7, 2006 now U.S. Pat. No. 8,308,749, entitled Catheter with Disruptable Guidewire Channel, which is a continuation-in-part of commonly owned U.S. patent application Ser. No. 10/346,599, filed on Jan. 17, 2003, entitled Catheter with Disruptable Guidewire Channel, now abandoned.

BACKGROUND OF THE INVENTION

1. Field of the Invention

The present invention relates to catheter systems for delivery of medical devices into a patient, and particularly to medical devices that are delivered to a treatment site using a guidewire.

2. Description of Related Art

Minimally invasive (or "interventional") medical procedures are commonly employed today to avoid the substantial effort and trauma inherent in traditional surgery. Instead of directly accessing a treatment site through surgical procedures, a physician will make a small incision into a remote vessel (e.g., a femoral artery) and guide the necessary tools to the treatment site using fluoroscopy or other visualization techniques. Access to the treatment site is first achieved using very low profile devices that can be "steered" through the various branches of vessels to the correct treatment location. Typically these initial small diameter devices will be a steerable guidewire or a small-diameter guiding catheter that is followed by insertion of a guidewire. Once in the correct position, treatment devices can then be attached to the guidewire and advanced to the treatment site along the guidewire like a train traveling along a track. Following treatment, each treatment device is then pulled out of the patient along the same guidewire to allow, if needed, further treatment devices to be advanced along the guidewire to the treatment site.

This basic approach is now used in a wide variety of medical procedures, including internal vessel repairs (e.g., repairing aneurysms in the aorta or other vessels using grafts or stent-graft devices) and treating blockages in vessels (e.g., performing balloon angioplasty or thrombectomy, and stent or stent-graft placements). All of these procedures tend to be much faster and far less traumatic than comparable surgical treatments. As a result, there are a host of benefits by using these procedures, including: fewer medical professionals need to attend the procedures; the procedures can be completed more rapidly; the patient may need far less extensive anesthesia and, where appropriate, can be awake and cooperative during the procedure; and since the trauma of open surgery is avoided overall hospital stays are dramatically reduced (e.g., for the repair of an abdominal aortic aneurysm hospital stays can be reduced from over a week including intensive care to only a couple of days or less).

Two basic categories of techniques are commonly used today to advance treatment apparatus to a treatment site along a guidewire. First, "over the wire" (OTW) techniques employ a long guidewire that extends far out of the patient's body. In the OTW procedures, each treatment device is mounted on a catheter that includes a guidewire lumen extending the entire length of the catheter. The physician threads each catheter completely over the length of the guidewire extending out of the patient and, while an assistant controls the tail end of the guidewire, the physician feeds the catheter to the treatment site. Following treatment, the entire catheter is then removed along the guidewire, again with the assistant controlling the tail end of the guidewire to keep it from moving out of position or touching the floor or other non-sterile areas. The OTW techniques have been widely practiced and provide very good trackability for the devices along the guidewire. However, these techniques require that the long tail end of the guidewire be controlled at all times, requiring at least one additional assistant throughout the procedure. Further, the threading of the entire length of the catheter along the guidewire can be somewhat difficult and time consuming. Moreover, limiting the speed with which procedures can be completed and the types of procedures that can be easily performed, these techniques require each treatment device to be completely retracted along the guidewire before a further treatment device can be advanced along the same guidewire to the treatment site.

The second common category of techniques for advancing treatment apparatus to a treatment site is commonly referred to as "rapid exchange" techniques. In rapid exchange procedures a guidewire lumen is provided over only a relatively short distal length of the treatment catheter, having a guidewire port exiting the catheter shaft next to or a short distance back from the treatment device. In this manner a relatively short guidewire can be employed that does not extend far from the patient's body. The physician advances the catheter over the guidewire (through the guidewire lumen) and gains control of the proximal end of the guidewire where it exits the catheter near the catheter's distal end. The physician can then guide the catheter into position without the need of an assistant controlling an extra long guidewire tail. Examples of such devices are described in U.S. Pat. Nos. 4,762,129 to Bonzel and 5,040,548 to Yock. Although the rapid exchange techniques may sacrifice some trackability in use, these techniques can allow for faster threading of each treatment device and cost savings in the elimination of extra long guidewires and one assistant to control the guidewire tail during the procedure. However, in practice these techniques also require each treatment device to be completely retracted along the guidewire before a further treatment implement can be advanced along the guidewire to the treatment site.

Other apparatus have been developed to provide some of the same benefits provided by the rapid exchange catheter techniques. For example, it has been suggested that the guidewire connect to the treatment catheter only at the distal tip of the guidewire, with a tube housing a guidewire lumen extending along the outside of the treatment device. Examples of these devices are described in U.S. Pat. Nos. 5,458,639 to Tsukashima et al. and 6,371,961 to Osborne et al. A similar device is taught in U.S. Pat. No. 6,394,995 to Solar et al. whereby an "advancement member" is provided attached to a treatment balloon; the advancement member includes a short tube at its far distal end forming a guidewire lumen. While these devices may deliver some of the same benefits of the conventional rapid exchange catheters, trackability may be a far greater problem since the guidewire is attached to the treatment catheter only at the very tip of the catheter. Additionally, depending upon the dimensions and stiffness of the tube housing the guidewire lumen (or, in the case of the Solar et al. device, of the "advancement member"), its presence on the outside of the treatment device may interfere with the proper operation of the treatment device. Finally, as was true with the other techniques discussed above, these devices would appear to require each treatment device to be completely retracted along the guidewire before a further treatment implement can be advanced along the guidewire to the treatment site.

It is accordingly a purpose of the present invention to provide an improved apparatus for advancement of a catheter along a guidewire that can be loaded and operated on a relatively short guidewire by a single operator.

It is a further purpose of the present invention for such an apparatus to provide a guidewire lumen that affords all necessary trackability while a treatment device is being advanced to a treatment site.

It is still a further purpose of the present invention for such an apparatus to allow other treatment devices to be advanced along the same guidewire without prior removal of the first treatment device.

These and other purposes of the present invention will become evident from review of the following description.

SUMMARY OF THE INVENTION

The present invention is an improved catheter device that includes a disruptable guidewire channel. The guidewire channel is configured to provide necessary trackability of the catheter along the guidewire during introduction of the catheter to a treatment site. Once treatment is completed, the guidewire channel can then be disrupted so as to free the guidewire from the catheter in situ.

In one embodiment of the present invention, it comprises a balloon and catheter assembly having an enlargeable balloon mounted on a catheter shaft. A sleeve is attached to the balloon forming a guidewire channel along at least a portion of the balloon. At an appropriate time, the sleeve may be disrupted to cause a guidewire placed within the sleeve to free from the balloon. The sleeve can be disrupted through a variety of means, including being formed from intentionally fragile material that will separate upon inflation of the balloon, having one or more separation lines (for example, perforations) pre-formed in the sleeve, having an attachment line between the sleeve and the balloon that is formed to split at an appropriate time, and having one of a variety of slots into which the guidewire can be placed and then remotely removed.

The present invention may be further defined as a guidewire deliverable treatment implement comprising a sleeve attached to the implement forming a guidewire channel along at least a portion of the implement. Again, the sleeve is disruptable to cause a guidewire placed within the sleeve to free, in whole or in part, from the implement upon disruption of the sleeve. Treatment implements that may be employed with the present invention may include: fluid-inflatable balloons; mechanically expandable balloons; catheters; catheter systems; stent delivery systems; stent-graft delivery systems; embolic filters; occluders; and other such devices.

The present invention may be still further defined as a medical device having a balloon configured for insertion within a patient's body directed along a guidewire and a guidewire channel attached to the balloon. The guidewire channel is formed from a material that maintains the guidewire close to the balloon during insertion and alters upon inflation of the balloon to separate the guidewire from the balloon upon subsequent deflation of the balloon. This separation of the guidewire from the balloon may take the form of various separation lines or other complete disruption means or may include a material that disrupts by distending away from the balloon so as to allow other devices to be advanced over the same guidewire past the balloon through the disrupted channel.

The apparatus of the present invention provides distinct advantages over existing over-the-wire and rapid exchange catheter introduction methods, including the ability to achieve much faster treatment implement exchanges, the ability to rapidly deliver multiple treatment implements in series, and the ability to maintain multiple treatment implements simultaneously at a treatment site using a single guidewire. These advantages can be realized by the present invention because: the catheter does not have to be axially removed prior to advancement of another catheter on the same guidewire; the catheter can remain across an initial lesion for future touch up, while another catheter is advanced to treat a distal lesion; and the catheter allows treatment of multiple stenotic lesions at a bifurcation requiring only one guidewire, thus eliminating entanglement of guidewires that can occur when utilizing multiple guidewires.

DESCRIPTION OF THE DRAWINGS

The operation of the present invention should become apparent from the following description when considered in conjunction with the accompanying drawings, in which:

FIG. 3 is an isometric view of the balloon catheter of FIG. 1, showing the balloon fully inflated and the guidewire channel disrupted;

FIG. 4 is an isometric view of a balloon catheter incorporating a guidewire channel of the present invention with a stent mounted over the balloon catheter and guidewire channel;

FIG. 5 is an isometric view of the balloon catheter and stent of FIG. 4, showing the balloon and stent fully expanded and the guidewire channel disrupted;

DETAILED DESCRIPTION OF THE INVENTION

The present invention is an improved apparatus for delivery of an interventional device along a guidewire to a remote treatment site in a patient's body.

As the terms "interventional" or "minimally invasive" devices or procedures are used herein they are intended to encompass any device or procedure whereby a medical treatment implement is delivered to a treatment site by use of wires and/or tubes threaded through vessels or other body passageways accessed remotely. Such devices may include those employed in: balloon angioplasty; thrombectomy; stent, graft, or stent-graft placement; embolic filter device placement; remote diagnostic procedures, such as those employing fiber optic cameras, ultrasound monitoring, MRI monitoring, x-ray monitoring, etc.; remote therapeutic procedures, such as those employing cutting blades, lasers, heat application, cold application, radiation, drug delivery, etc.; and any other similar devices or procedures now known or later developed. Currently such interventional procedures are employed in large and small blood vessels, in other vessels in the body, such as in the bile duct, as well as in the respiratory, digestive, reproductive, and other body systems. As the term "patient" is used herein it is intended to encompass both humans and animals.

As the term "guidewire" is used herein it is intended to encompass any device that provides a track for guiding medical implements to a treatment site in a minimally invasive procedure. Such devices may include straight, coiled, braided, coated, or other forms of wires, various tubular devices, such as catheter tubes, hypo-tubes, balloon-on-wire devices, and the like, or any other form of similar elongated device.

Figure 1:
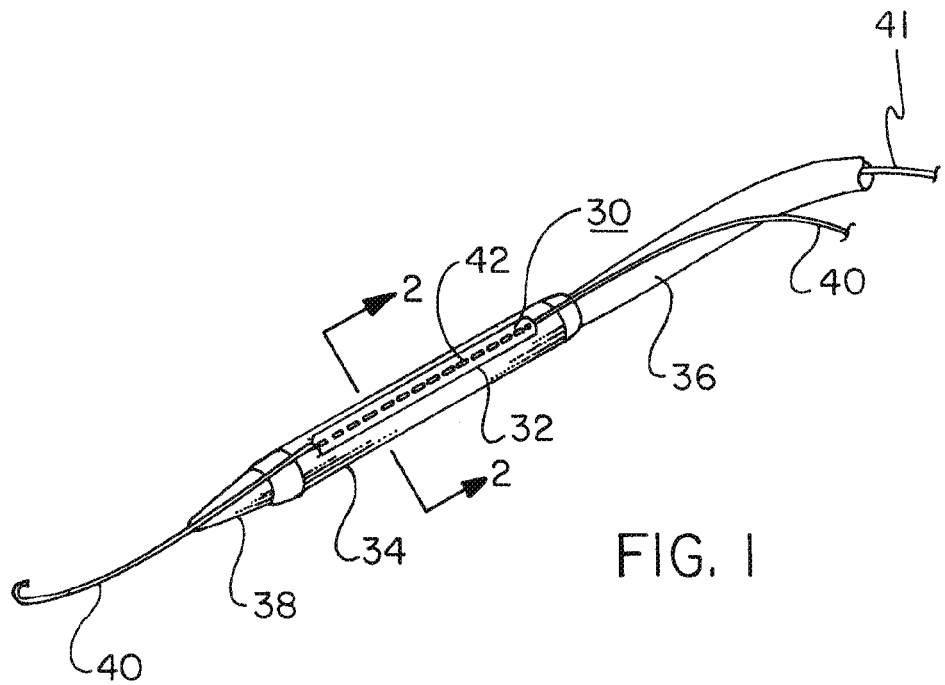
FIG. 1 is an isometric view of a balloon catheter incorporating one embodiment of a guidewire channel of the present invention.
Figure 2:
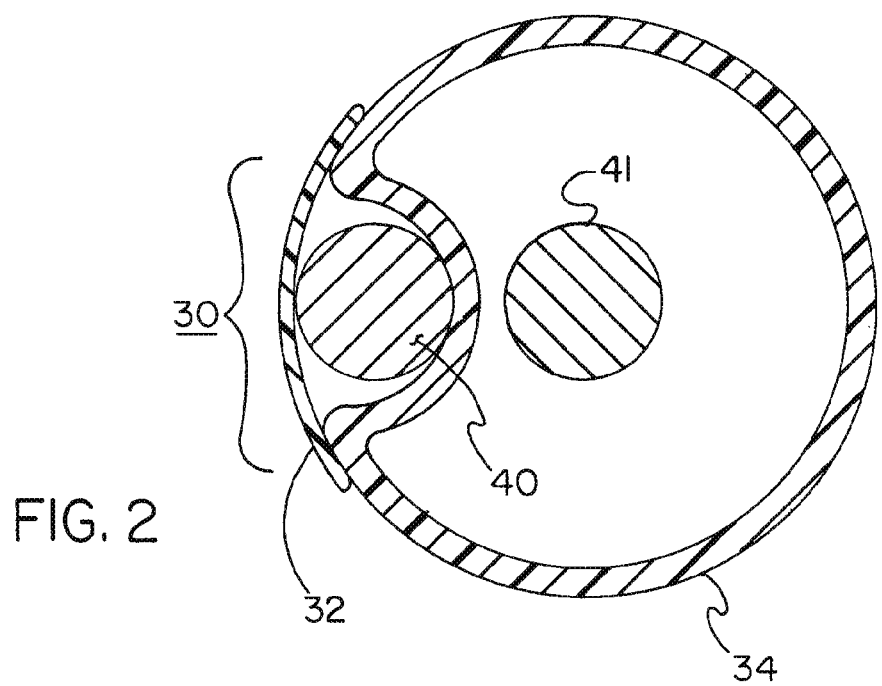
FIG. 2 is cross-section view of the balloon catheter and a guidewire channel along line 2-2 of FIG. 1.

Referring to the illustrations, FIGS. 1 and 2 show one embodiment of a guidewire channel 30 of the present invention. The guidewire channel 30 comprises a sleeve 32 attached to a treatment implement 34, in this case an expandable balloon 34, mounted on a catheter shaft 36. The catheter shaft 36 includes a distal end 38 and a proximal end (not shown) extending out of the patient's body. The guidewire channel 30 is proportioned to slidably receive a guidewire 40 therein. The catheter shaft 36 should be stiff enough to allow the balloon 34 to be advanced along the guidewire 40 by the physician pushing on that portion of the catheter shaft 36 extending outside of the patient's body.

If the catheter tube alone does not provide sufficient longitudinal stiffness, a reinforcement wire 41 or similar support member may be incorporated into the catheter shaft 36 to aid in its pushability. The support member can be combined with the catheter in a variety of ways, including being attached distally to the catheter shaft distal to the balloon, being attached to the catheter shaft proximal to the balloon, or being unattached to the catheter shaft distally. In an unattached configuration, the support member can provide pushability when held by compressive forces of a stent mounted over the guidewire or similar constraining means. The support member can be attached proximally, such as to the catheter shaft or the hub.

It is important that the treatment implement tracks closely along the guidewire while the catheter is being advanced to a treatment site in a body. This is particularly important when a treatment site is in small vessels, such as coronary arteries, that may have numerous branch vessels located nearby. As such, the guidewire channel should be proportioned to keep the treatment implement closely aligned with the guidewire during device advancement through the body while not overly constricting movement of the treatment implement along the guidewire. However, the present inventor has realized that once the treatment implement is correctly positioned within the treatment site and treatment has occurred, there is no reason why the treatment implement must remain on the guidewire for its subsequent removal from the body.

As such, the guidewire channel 30 of the present invention includes means to "disrupt" the channel at an appropriate time so as to separate the treatment implement 34 from the guidewire 40. In the embodiment illustrated in FIGS. 1 and 2, such means 42 comprises a separation line comprising a line of perforations formed along the length of the sleeve 32. As is shown in FIG. 3, when the balloon 34 is expanded, the sleeve 32 disrupts along the separation line, freeing the guidewire 40 from the constraint of the guidewire channel. The sleeve 32 can occupy all or a portion of the balloon circumference.

In this manner, the guidewire channel 30 provides the necessary guidance while the treatment implement is being advanced into the body, but effectively disappears when guidance is no longer required so that the treatment implement can be removed independently of the guidewire. Unlike previous interfaces between catheters and guidewires, in situ separation of a first treatment implement from the guidewire immediately makes the guidewire available for the advancement of further treatment implements to the treatment site or to another adjacent or distal treatment site. This provides the physician with numerous options that are not currently available, such as allowing a second treatment implement to be advanced along the guidewire while a first treatment implement is either left in place or is being simultaneously removed, and/or allowing multiple treatment implements to be mounted in series on a single guidewire, with each advanced and used without the need to immediately and completely remove the previous treatment device.

It should be evident that this construction circumvents the need for a long guidewire and extra medical personnel required with OTW catheters, while permitting far easier and quicker catheter exchanges than are possible with current so-called "rapid exchange" catheter systems.

For most embodiments of the present invention, the sleeve 32 should be formed from a relatively thin material that is selected and/or treated to disrupt at the appropriate time upon inflation of the balloon 34. A sleeve of the present invention may be constructed from a wide variety of materials, including PTFE, expanded PTFE, polyamide, polyether block copolymers and other copolymers, polyurethane, ethylene vinyl acetate (EVA), polyvinylchloride (PVC), poly(ethylene terephthalate) (PET), PETG, polyethylene, silicone, latex, etc., as well as composites or various combinations thereof. The sleeve can be attached to virtually any form of balloon material, including balloons made from any of the above listed materials. The balloon material may be elastic or inelastic, and compliant, non-compliant, or semi-compliant. One suitable balloon material that may be used with the present invention comprises a composite balloon of expanded PTFE and elastomer, such as the balloons described in U.S. Pat. Nos. 5,752,934, 5,868,704, 6,120,477, all to Campbell et al.

Attachment of the sleeve to the balloon may take any suitable form, such as through adhesive, heat welding, ultrasonic welding, or other bonding method. The sleeve material should be thermally compatible with the balloon material if heat bonding is the means of attachment. The preferred sleeve material should have minimal thickness of less than about 0.003 inches (about 0.08 mm), and more preferably a thickness of between about 0.001 to about 0.002 inches (about 0.02 to 0.05 mm). A minimal thickness of the sleeve is preferred in that it is desirable that the guidewire channel not interfere with the normal operation of the treatment implements.

As the term "sleeve" is used herein, it is intended to encompass any configuration of material that forms a channel through which a guidewire will be retained in close proximity to a catheter shaft during device advancement through a body while allowing the catheter shaft to slide relative to the guidewire. A sleeve of the present invention may comprise one or more strips of material that is attached to a balloon or other treatment implement, or it may comprise one or more tubes of material that surrounds the balloon or other treatment implement, or it may comprise a guidewire retainer inside a balloon. Regardless of configuration, the sleeve of the present invention should provide a guidewire channel that is "disruptable."

As is explained and illustrated in greater detail below, as the terms "disrupt" or "disruptable" are used in reference to the guidewire channels of the present invention they are intended to encompass any guidewire channel that breaks, separates, distends, or otherwise releases the guidewire from a treatment implement to allow another treatment implement to be advanced along the same guidewire without removal of the prior treatment implement. Disruptable guidewire channels of the present invention may include ones that are attached to the balloon material, integral with the balloon material, or folded within the balloon material.

FIGS. 4 and 5 illustrate how the above-described device may be used to deliver a deployable device, such as a stent. As is shown in FIG. 4, a stent 44 may be mounted over the previously described balloon 34 and guidewire channel 30 of the present invention. In this embodiment the guidewire 40 passes through the guidewire channel 30 under the stent 44.

FIG. 5 shows that upon inflation of the balloon 34, the stent 44 will expand to its deployed diameter while the guidewire channel 30 disrupts beneath the stent 44. Once the balloon 34 is deflated, the guidewire 40 will be separated from the balloon, allowing removal of the catheter 36 independent of the guidewire.

Figure 6:
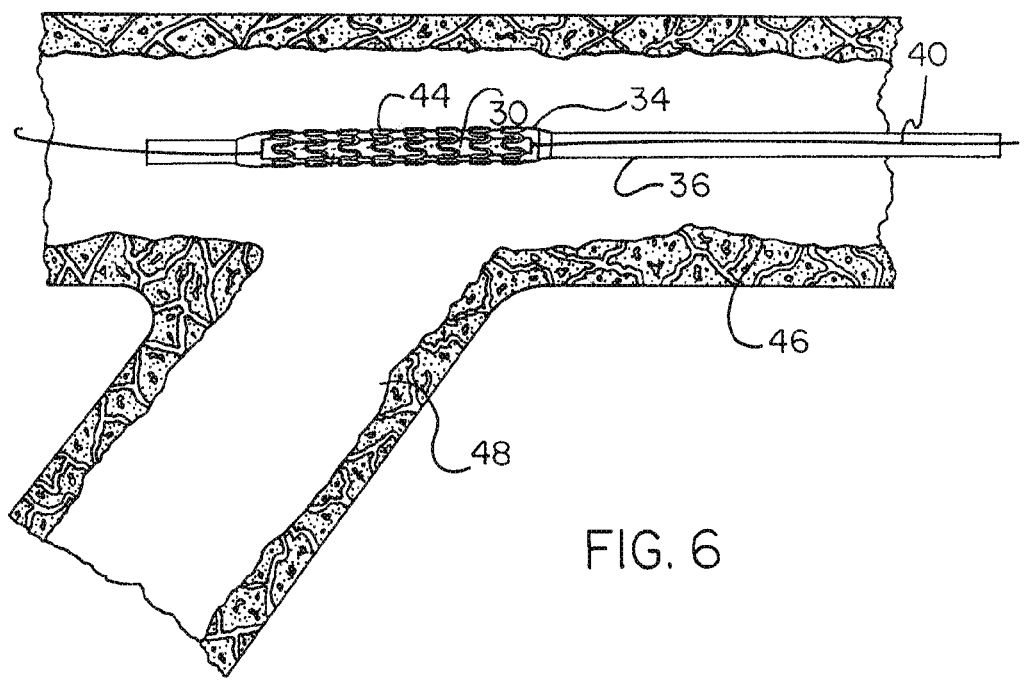
FIG. 6 is a side view of the balloon catheter and stent of FIG. 4 positioned in a patient's body at the junction of two blood vessels shown in cross-section.
Figure 7:
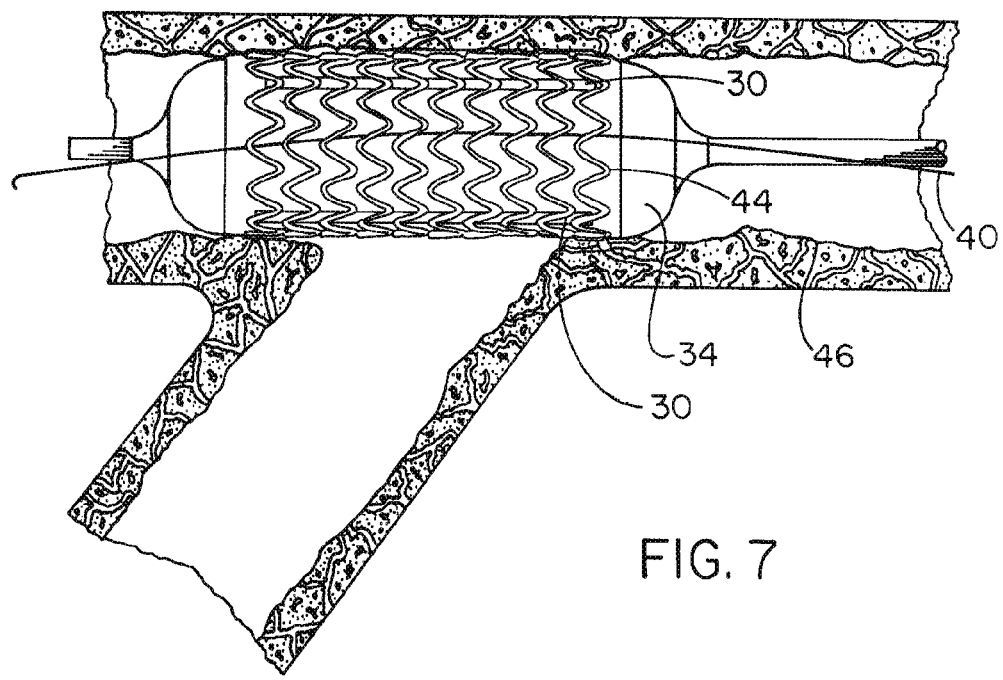
FIG. 7 is a side view of the balloon catheter and stent positioned in the blood vessel as shown in FIG. 6, showing the balloon and stent fully expanded.
Figure 8:
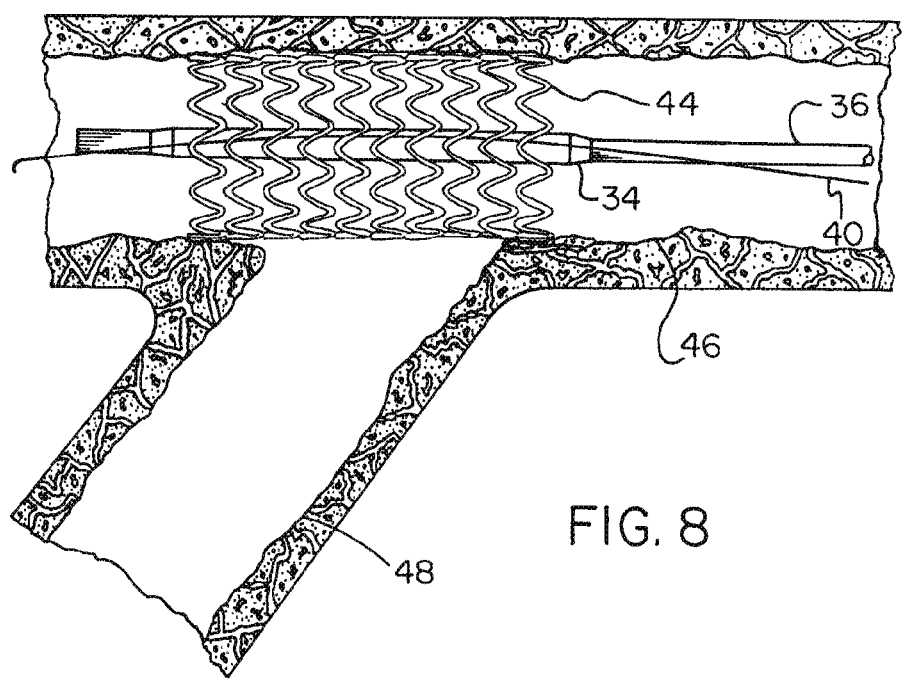
FIG. 8 is a side view of the balloon catheter and stent positioned in the blood vessel as shown in FIG. 7, showing the balloon catheter deflated and the stent positioned fully expanded within the blood vessel.

FIGS. 6 through 8 demonstrate the procedure for deploying the construct of FIGS. 4 and 5 in a blood vessel. FIG. 6 shows the balloon catheter 36 (incorporating the guidewire channel 30 of the present invention) and stent 44 of FIG. 4 positioned in a patient's body at the junction of a main vessel 46 and a branch vessel 48. FIG. 7 shows the balloon 34 and stent 44 fully expanded in the main vessel 46, with the guidewire channel 30 disrupted underneath the stent 44. FIG. 8 shows the balloon 34 fully deflated and the stent 44 positioned fully expanded within the main vessel 46. The guidewire 40 is now completely separated from the balloon 34 and catheter 36.

Figure 9:
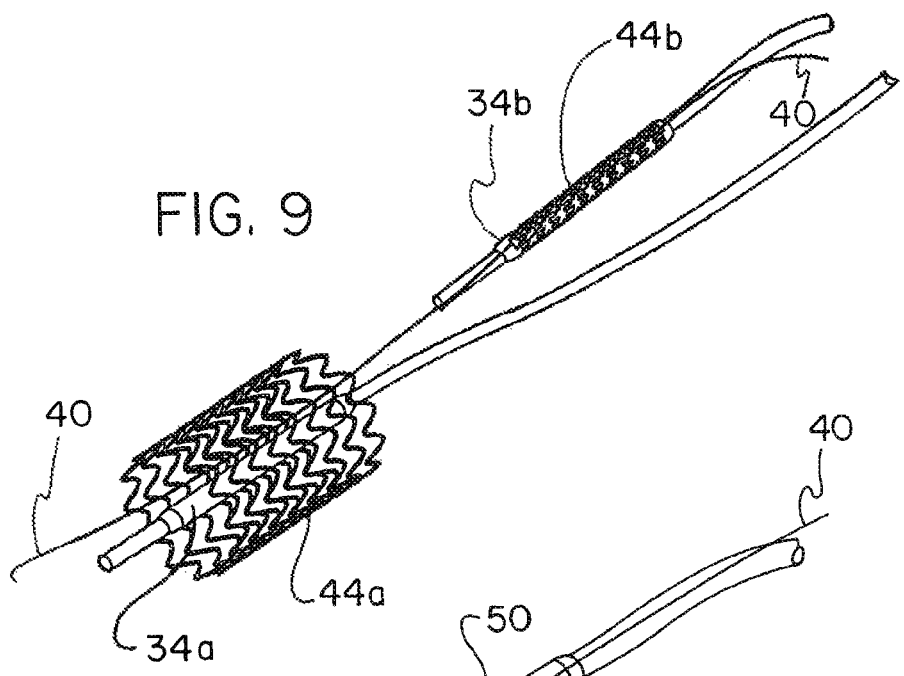
FIG. 9 is an isometric view of a second balloon catheter and stent being advanced along a guidewire following expansion of a first stent having been deployed on the same guidewire.

Once the guidewire 40 is separated from the balloon 34, additional devices can then be advanced on the guidewire 40 in order to accomplish further treatments. For example, FIG. 9 shows a second balloon 34b device of the present invention being advanced over the guidewire 40 with the original balloon device 34a left in place to accomplish further treatments. In this instance, two stents 44a, 44b may be deployed end-to-end (or overlapping) to address an extended defect in a vessel, with both balloons 34a, 34b kept in their original deployment positions to facilitate final "touch up" of stent placement prior to removal of the balloons.

In another embodiment of the present invention, a second stent can be advanced even further distal to the first stent in order to treat another defect. This problem can present itself when fluoroscopy fails to detect the second distal defect prior to treatment of the first defect. Maintaining the first implement across the first defect allows subsequent treatment (for instance, further distension of the first stent) to occur after treating the second distal defect.

Figure 10:
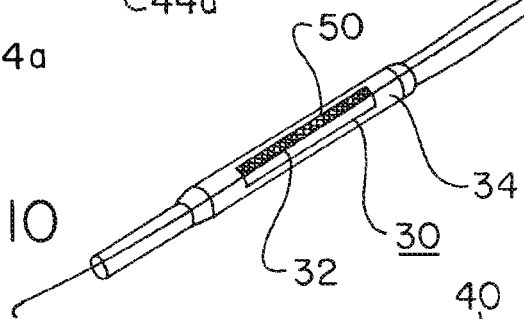
FIG. 10 is an isometric view of a balloon catheter incorporating another embodiment of a guidewire channel of the present invention.
Figure 11:
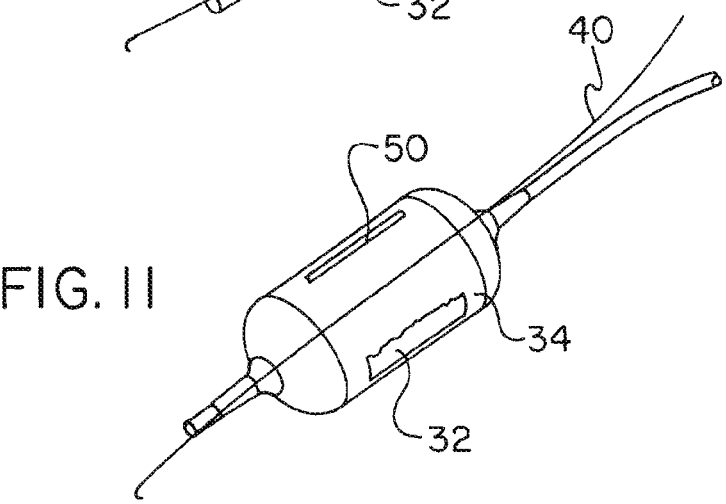
FIG. 11 is an isometric view of the balloon catheter of FIG. 10, showing the balloon fully inflated and the guidewire channel disrupted.

A further embodiment of the present invention is shown in FIGS. 10 and 11. In this embodiment the guidewire channel 30 is formed from a sleeve 32 that has a separation line comprising an intentionally loose attachment line 50 to the balloon 34. When the balloon is inflated, as is shown in FIG. 11, the loose attachment line 50 will separate from the balloon 34, freeing the guidewire 40. Loose attachment of the sleeve 32 to the balloon 34 may be accomplished through a variety of means, including use of weak adhesive, discontinuously applied adhesion points, perforations, weak sleeve material along the attachment line, weak weld (e.g., weak heat bond), etc.

Figure 12:
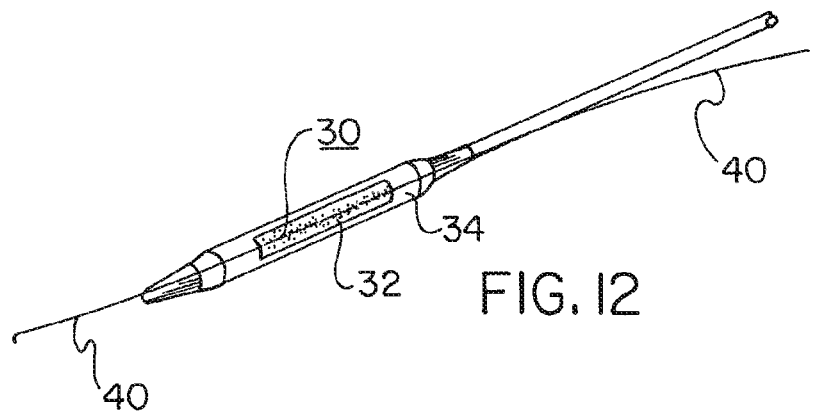
FIG. 12 is an isometric view of a balloon catheter incorporating still another embodiment of a guidewire channel of the present invention.
Figure 13:
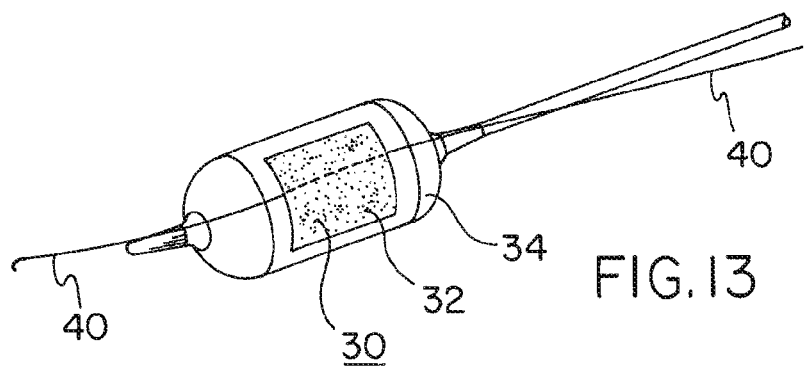
FIG. 13 is an isometric view of the balloon catheter of FIG. 12, showing the balloon fully inflated and the guidewire channel disrupted through distension.
Figure 14:
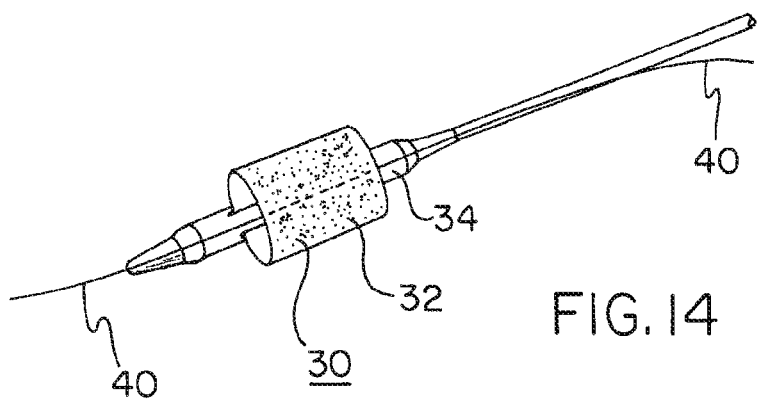
FIG. 14 is an isometric view of the balloon catheter of FIG. 13, showing the balloon deflated and the guidewire channel remaining disrupted through distension.

A further variation on the present invention is illustrated in FIGS. 12 through 14. In this embodiment the guidewire channel 30 comprises a sleeve 32 of distensible material that expands along with the balloon 34 and then has little or no recoil to its original dimensions following balloon 34 deflation. Although this configuration does not completely separate the guidewire 40 from the guidewire channel 30 following deployment, the guidewire channel 30 is still disrupted in that other devices can be advanced past the deflated first balloon 34 through the distended sleeve material. Suitable distensible material for use in this embodiment may include any material that can be distended beyond its elastic limit so as to present permanent plastic deformation.

Figure 15:
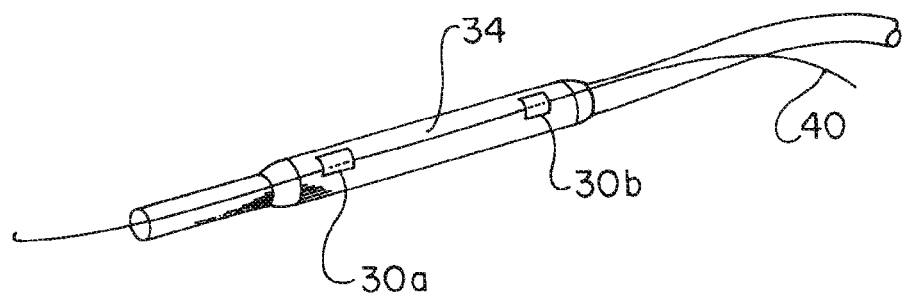
FIG. 15 is an isometric view of still another embodiment of the present invention comprising multiple separate guidewire channels.

A further embodiment of the present invention is shown in FIG. 15. In this embodiment, multiple separate guidewire channels 30a, 30b are attached to the treatment implement 34. Each of the guidewire channels 30a, 30b may include one or more of the previously described disruption means so as to free the guidewire 40 from the treatment implement 34 at the appropriate time. This embodiment may be preferable under certain circumstances where it is desirable to further limit the amount of material comprising the guidewire channel. It should be evident that this embodiment may be practiced with two, three, four, five, or more separate guidewire channels 30. Additionally, it should be understood that the separate guidewire channels of this embodiment may be of dimensions and properties identical to each other, or may differ from each other in dimensions, materials, attachment means, disruption means, and/or other properties.

Figure 16:
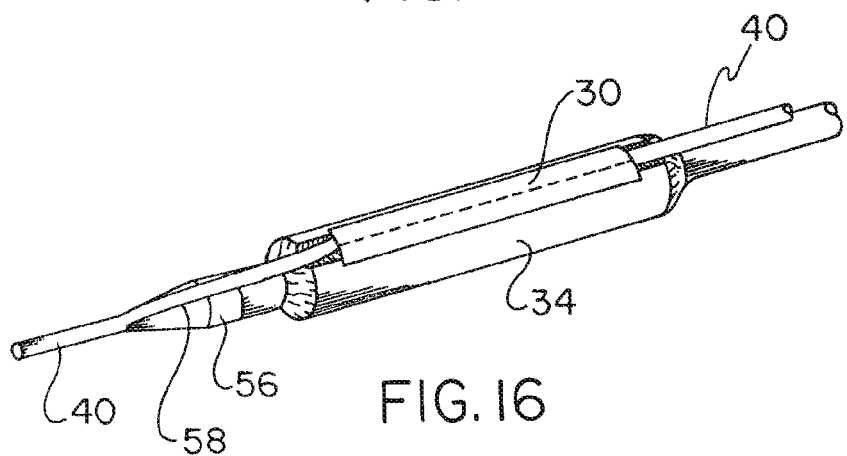
FIG. 16 is an isometric view of another embodiment of a balloon catheter of the present invention, employing a guidewire channel along with catheter tip including a guidewire centering groove.
Figure 17:
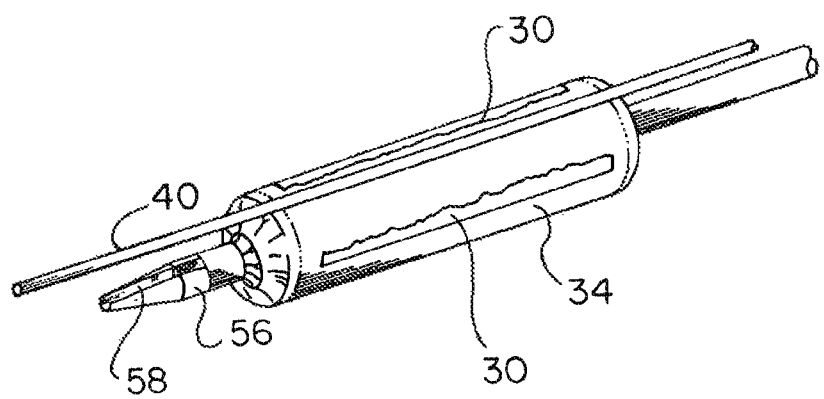
FIG. 17 is an isometric view of the balloon catheter of FIG. 16, showing the balloon fully inflated, the guidewire channel disrupted, and the guidewire separated from the centering groove in the catheter tip.

FIGS. 16 and 17 illustrate another embodiment of the present invention that employs both a disruptable guidewire channel 30 attached to the treatment implement 34 and a unique catheter tip 56. The disruptable guidewire channel 30 may be of any other forms described herein. The catheter tip 56 includes a guidewire centering groove 58 therein that is adapted to receive and retain a guidewire 40 in sliding fit during device loading and advancement to a treatment site. The centering groove 58 provides an additional anchorage for the guidewire to the treatment implement during device advancement and may be used to improve the trackability and crossability of the device. The centering groove 58 is proportioned to release the guidewire 40 from the tip 56 when the treatment implement 34 is expanded, as is shown in FIG. 17. Preferably the tip 56 and centering groove 58 are formed from the same or similar material as the balloon or catheter shaft material, such as thermoplastic material used in medical devices (e.g., polyamide, polyurethane, PTFE, polyethylene, EVA, PVC, etc.).

Figure 18:
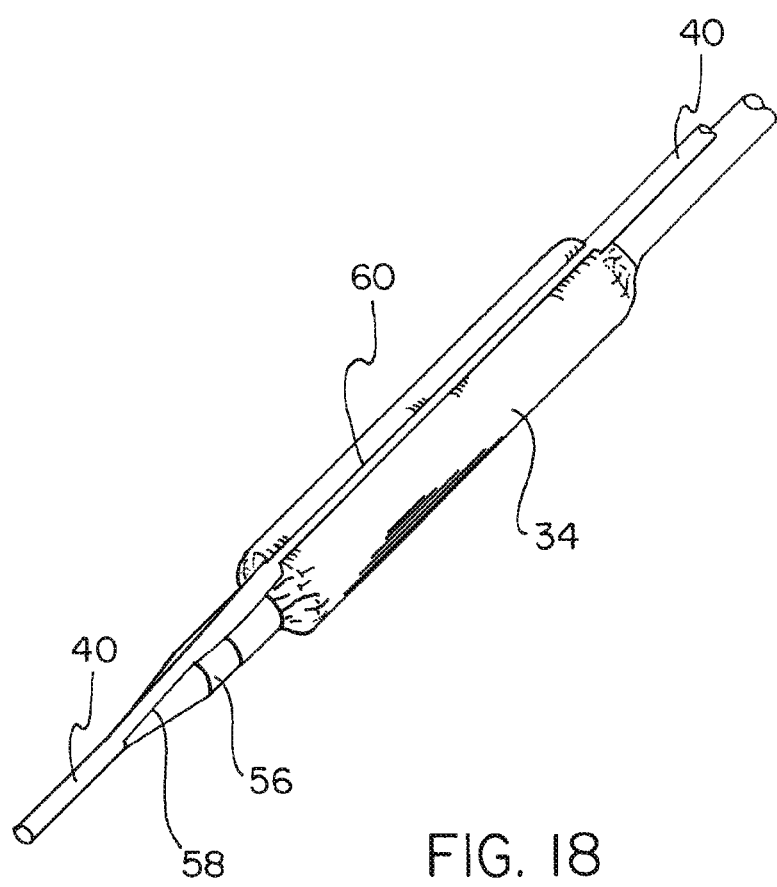
FIG. 18 is an isometric view of a further embodiment of a balloon catheter of the present invention comprising a disruptable channel formed in the balloon itself and employing a catheter tip with a guidewire centering groove.
Figure 19:
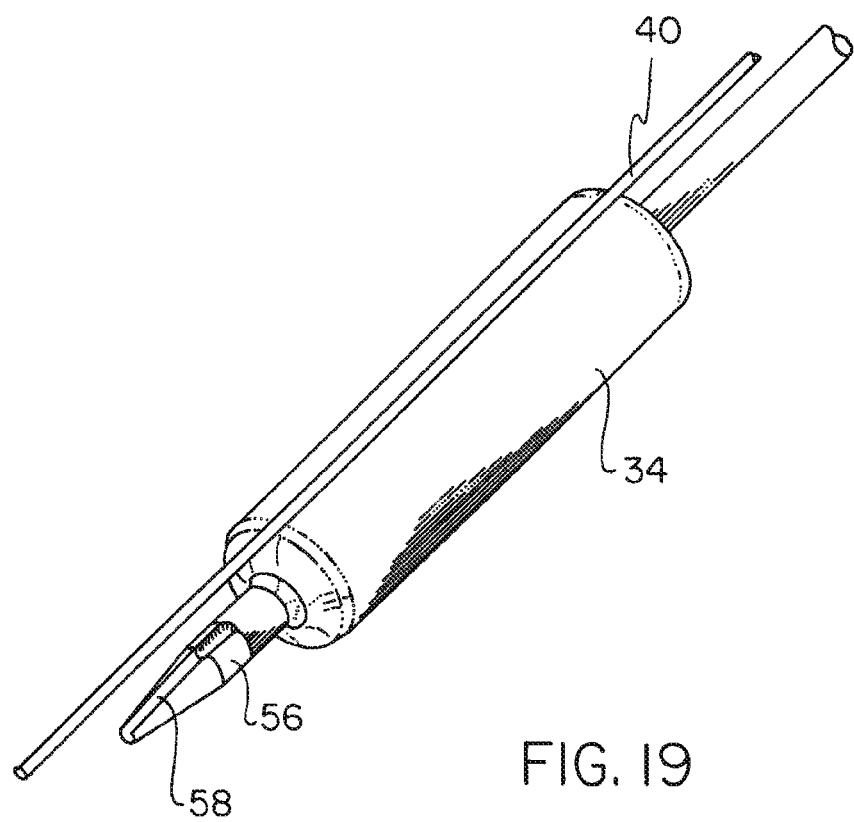
FIG. 19 is an isometric view of the embodiment of FIG. 18, showing the balloon fully inflated, releasing the guidewire from the channel formed in the balloon, and the guidewire separated from the centering groove in the catheter tip.

A similar application of the present invention is shown in FIG. 18. In this embodiment, a disruptable channel 60 is formed from the external surface of the balloon 34 itself. Again, a tip 56 with a centering groove 58 is employed to aid in guidewire 40 attachment, trackability and crossability during device advancement. As is shown in FIG. 19, when the balloon 34 is expanded, the disruptable channel 60 disappears, releasing the guidewire 40 from attachment to the balloon 34. The guidewire 40 will likewise separate from the centering groove 58.

Figure 20:
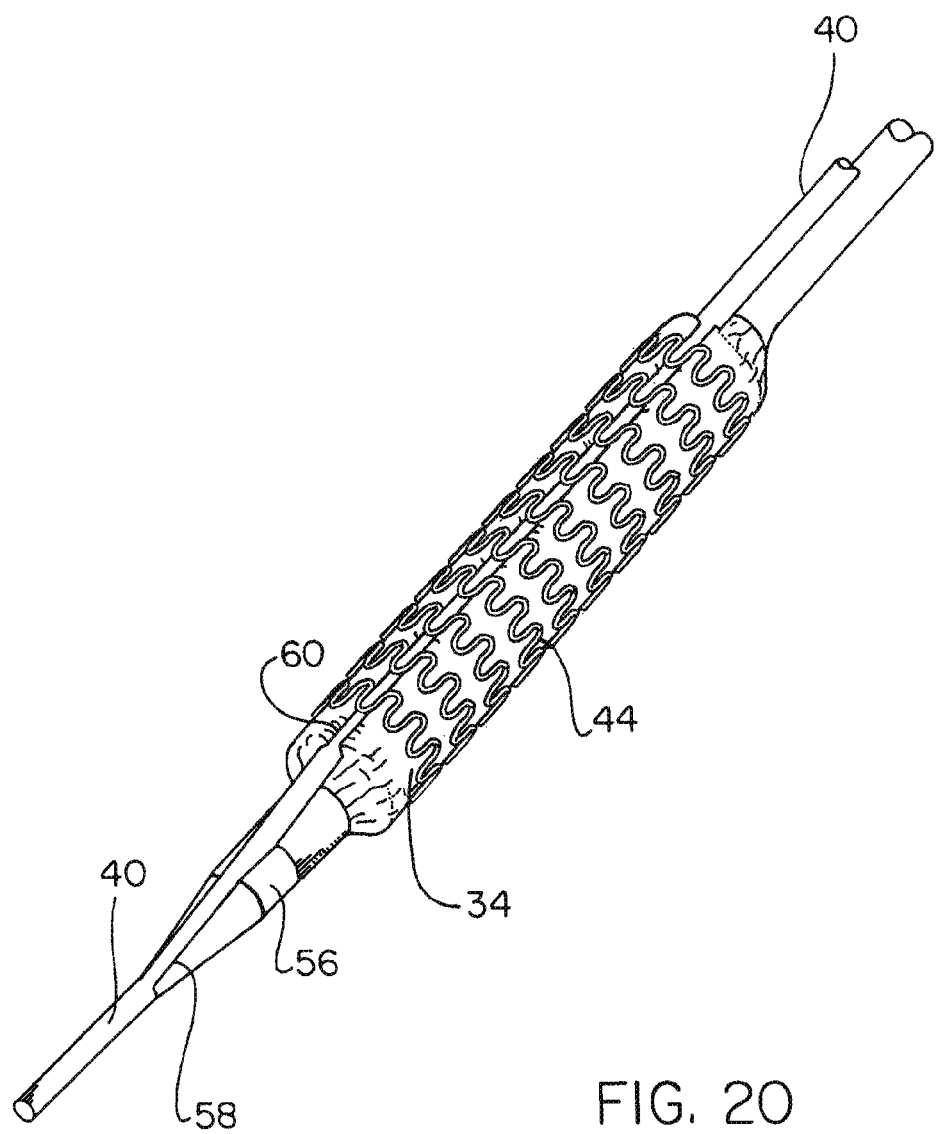
FIG. 20 is an isometric view of the embodiment of FIG. 18 including a stent mounted over the balloon.

FIG. 20 illustrates how the embodiment of FIGS. 18 and 19 can be used to deliver a deployable device 44. The disruptable channel 60 should be formed of sufficient dimensions and structural integrity so that the deployable device 44 can be adequately attached to the balloon 34 without hindering the proper sliding motion of the guidewire 40 through the disruptable channel 60 during device advancement.

Figure 21:
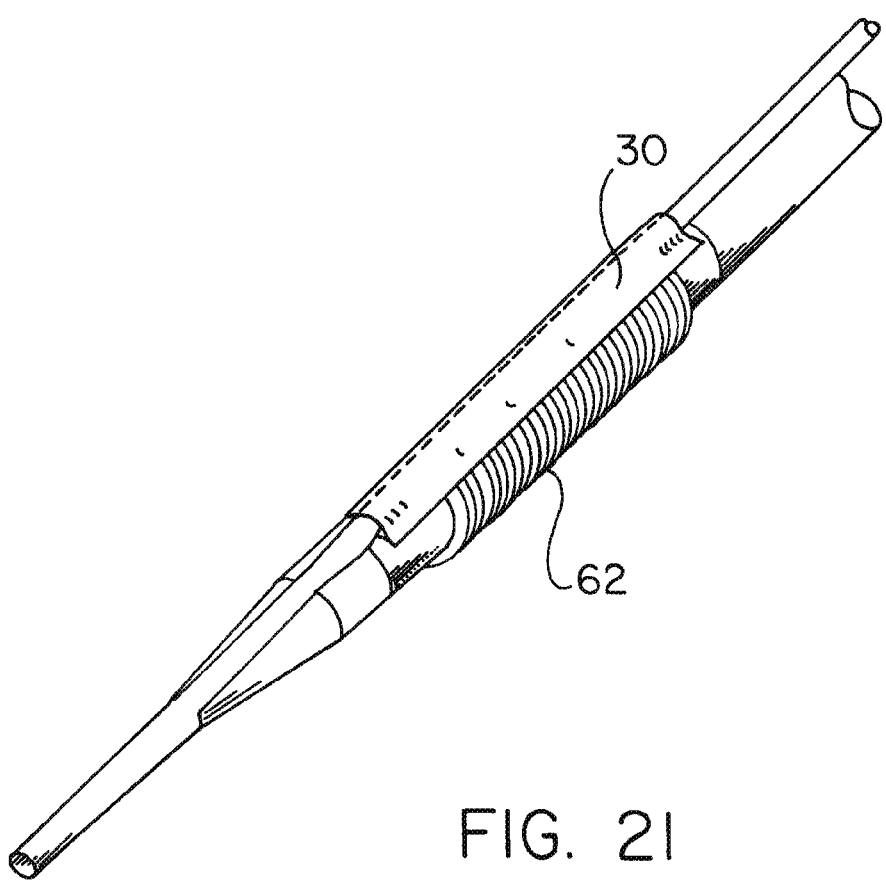
FIG. 21 is an isometric view of a further embodiment of the present invention employing a guidewire channel on a mechanical balloon.

FIG. 21 shows how the present invention may be adapted to be used with other treatment apparatus beyond inflatable balloons. In this embodiment, a guidewire channel 30 of the present invention is attached to a mechanical expansion device 62, adapted to expand upon mechanical actuation instead of introduction of fluid pressure. Other treatment implements that may benefit from use with a guidewire channel of the present invention may include, without limitation: other fluid-inflatable balloons; mechanically expandable balloons; catheters; catheter systems; stent delivery systems; stent-graft delivery systems; embolic filters; occluders; and other such devices.

Figure 22:
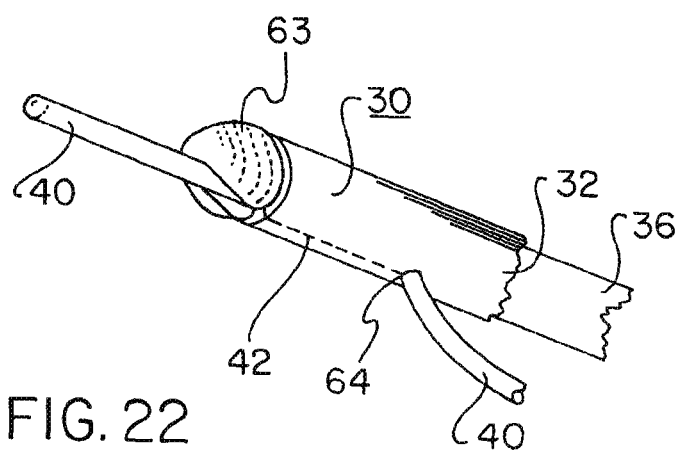
FIG. 22 is an isometric view of a still further embodiment of the present invention employing a guidewire channel with perforated tear release.
Figure 23:
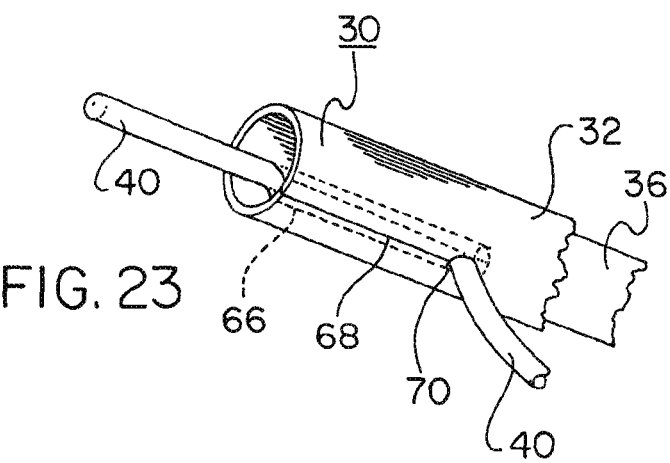
FIG. 23 is an isometric view of another further embodiment of the present invention employing a guidewire channel with a slit release.
Figure 24:
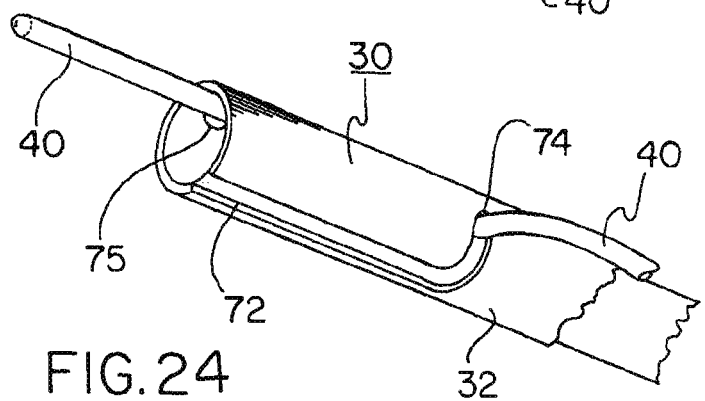
FIG. 24 is an isometric view of still another embodiment of the present invention employing a guidewire channel that has a slot allowing for rotational release.

FIGS. 22 through 24 illustrate embodiments of the present invention that can release from the guidewire without need for an inflation device to disrupt the sleeve.

FIG. 22 demonstrates that the guidewire channel 30 of the present invention may be formed from a tubular sleeve 32 that completely surrounds the treatment implement 34 and includes a tear line 42. In this embodiment, the sleeve is slidable relative to a coaxial underlying catheter shaft 36 (for instance, the tubular sleeve 32 may extend along the entire length of the catheter 36 to allow the sleeve and the catheter to be moved relative to one another). If an inflatable member is not employed, an enlarged bulb member 63 can be mounted on the catheter shaft 36. By actuating the catheter shaft 36 relative to the tubular sleeve 32 (by either pulling the catheter or pushing the tubular sleeve, or both), the bulb member 63 can disrupt the tear line 42, freeing the guidewire 40 from the guidewire channel 30. Additionally, this embodiment further demonstrates that the guidewire 40 does not have to traverse the entire length of the sleeve 32, but may be adapted to exit the sleeve 32 through a port 64 provided along its length. In this manner, the sleeve 32 does not have to tear along its entire length in order to release the guidewire 40.

FIG. 23 illustrates another disruption means for use with the present invention. In this embodiment the guidewire channel 30 comprises a tubular sleeve 32 formed from a resilient material with a resealable slit 68 and an exit port 70. An inner member contains a groove or passageway 66 extending from the distal tip and terminating at an outer member exit port 70. A guidewire 40 is fed through the passageway 66 at the time of device introduction. At the time of deployment, the resilient material of the sleeve 32 will part along the slit 68, releasing the guidewire from the passageway 66. Proximal displacement (pulling) of the outer member, or distal displacement (pushing) of the inner member, or some combination of the two, will release the guidewire.

Still another embodiment of the present invention is shown in FIG. 24. In this embodiment, the guidewire channel 30 is formed from a sleeve 32 having a rotational slot 72 formed therein. The guidewire 40 can be mounted into the channel by threading it through the sleeve 32 within a groove 75 of the inner member and out port 74, or by positioning the guidewire 40 along the length of the slot 72 and then pressing the guidewire 40 into the slot while the sleeve 32 is rotated to align the guidewire 40 within the sleeve 32 and exit the sleeve 32 through port 74. The sleeve 32 in this embodiment may be formed from a disruptable material, as previously described, or the guidewire can be released from the guidewire channel 30 by rotating the sleeve 32 at the appropriate time to align the groove 75 with the slot 72 and allow the guidewire to "pop" free from the slot 72.

Embodiments of the present invention that can be utilized without a balloon, such as those illustrated in FIGS. 22 through 24, have numerous possible applications, including without limitation, use with self-expanding stents, embolic filter devices, septal defect occlusion devices, etc.

Figure 25:
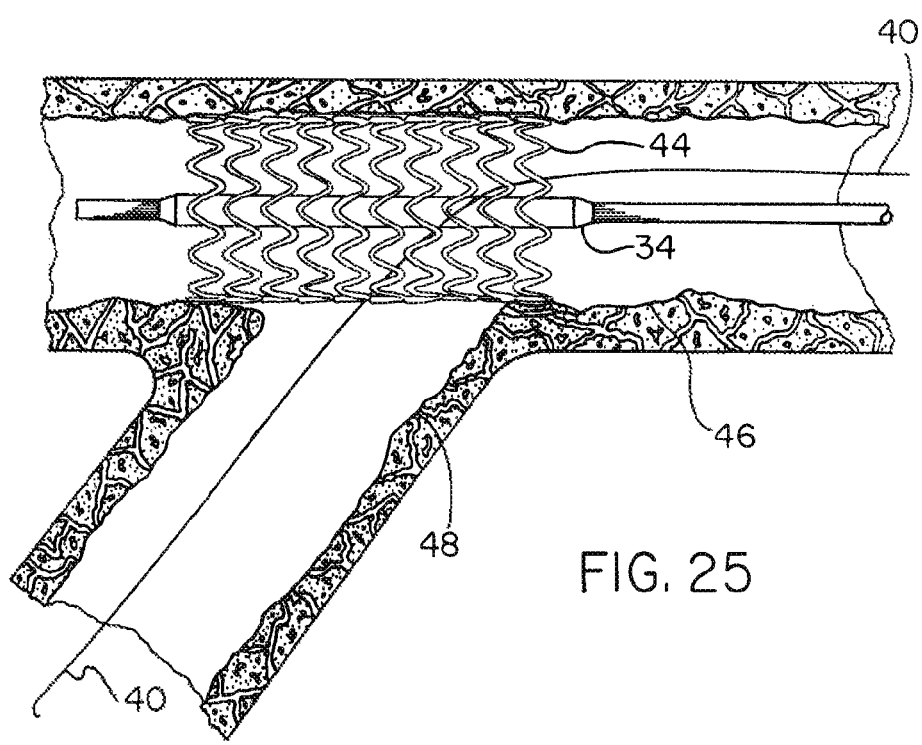
FIG. 25 is a side view of a stent placement in a branched vessel following the procedure illustrated in FIGS. 6 through 8 with the guidewire repositioned into the branch vessel through the interstices of the stent.

As has been noted, among the advantages of the present invention is the fact that a physician is provided with unique treatment options not presently available using conventional catheter delivery devices. One such unique procedure is illustrates in FIGS. 25 through 29. FIG. 25 shows the stent placement in a main vessel 46 illustrated in FIGS. 6 through 8, with the balloon 34 left in place as shown in FIG. 8. If a physician would now like to likewise provide a stent in the branch vessel 48, under currently available procedures s/he would have to either remove the first balloon 34 and then direct a second deployment device down the same guidewire 40, or laboriously thread a second guidewire into the branch vessel 48.

Figure 26:
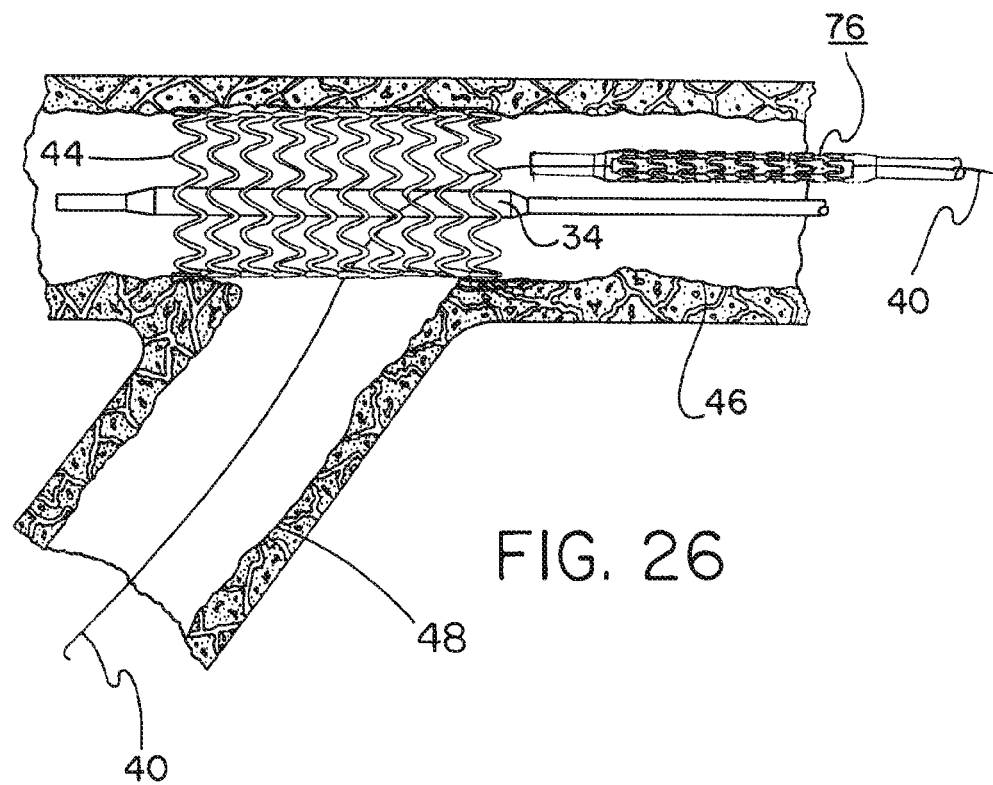
FIG. 26 is a side view of the stent placement of FIG. 25 showing a second balloon catheter of the present invention being advanced along the guidewire.
Figure 27:
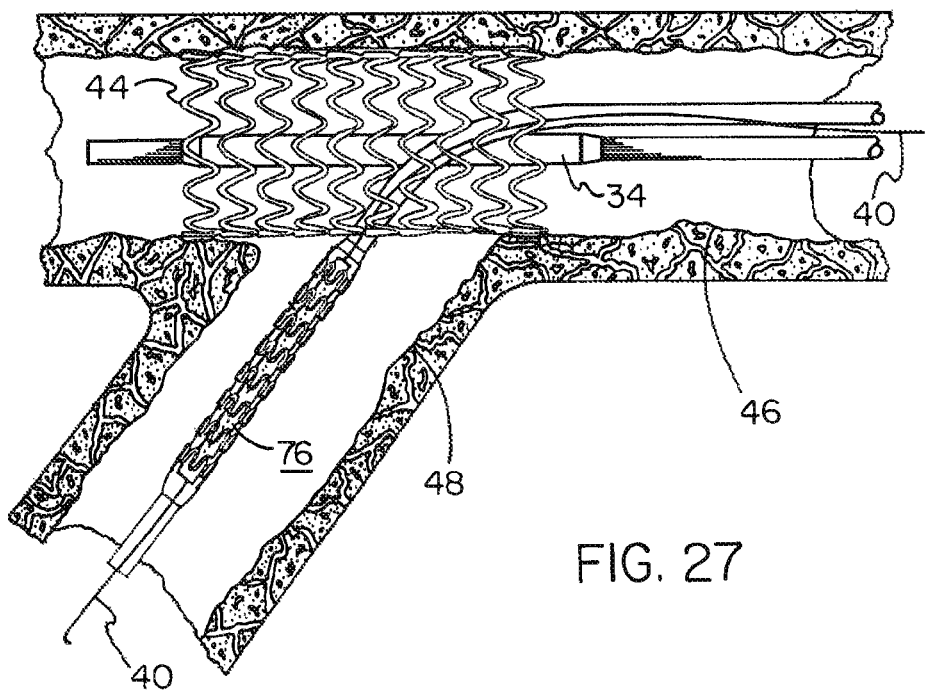
FIG. 27 is a side view of the stent placement of FIG. 26 showing the stent and balloon catheter positioned within the branch vessel.

With the present invention, however, since the guidewire 40 has been released from the balloon 34 in the procedure described in FIGS. 6 through 8, the guidewire 40 is now free to be repositioned into the branch vessel 48, as is illustrated in FIG. 25, while leaving the balloon 34 in position within the main vessel 46. A second deployment apparatus 76 can then be advanced along the guidewire 40, as is shown in FIG. 26, and positioned into the branch vessel 48, as is shown in FIG. 27.

Figure 28:
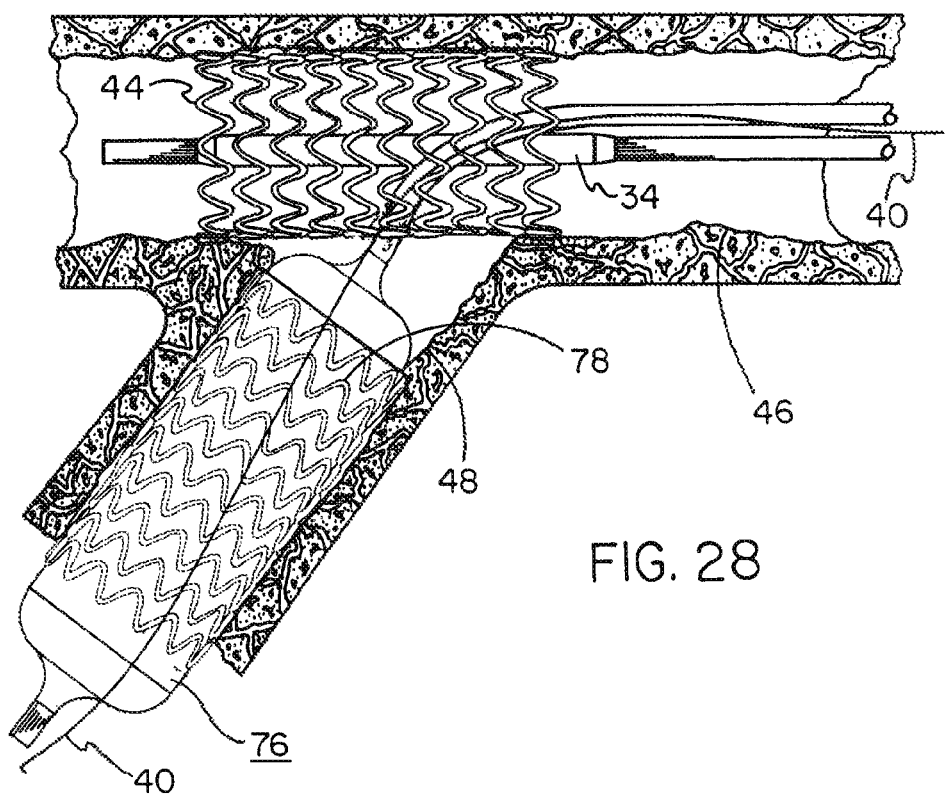
FIG. 28 is a side view of the stent placement of FIG. 27 showing the stent and balloon catheter fully inflated within the branch vessel.
Figure 29:
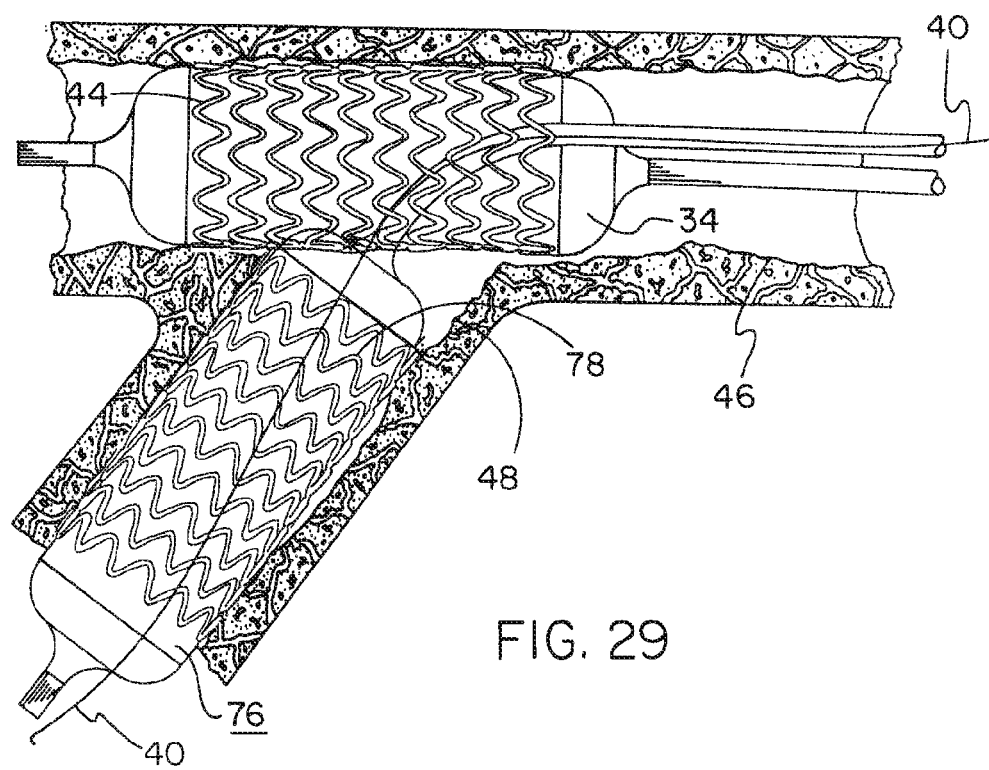
FIG. 29 is a side view of the stent placement of FIG. 28 showing both the balloon in the main vessel and the balloon in the side vessel fully inflated.
Figure 30:
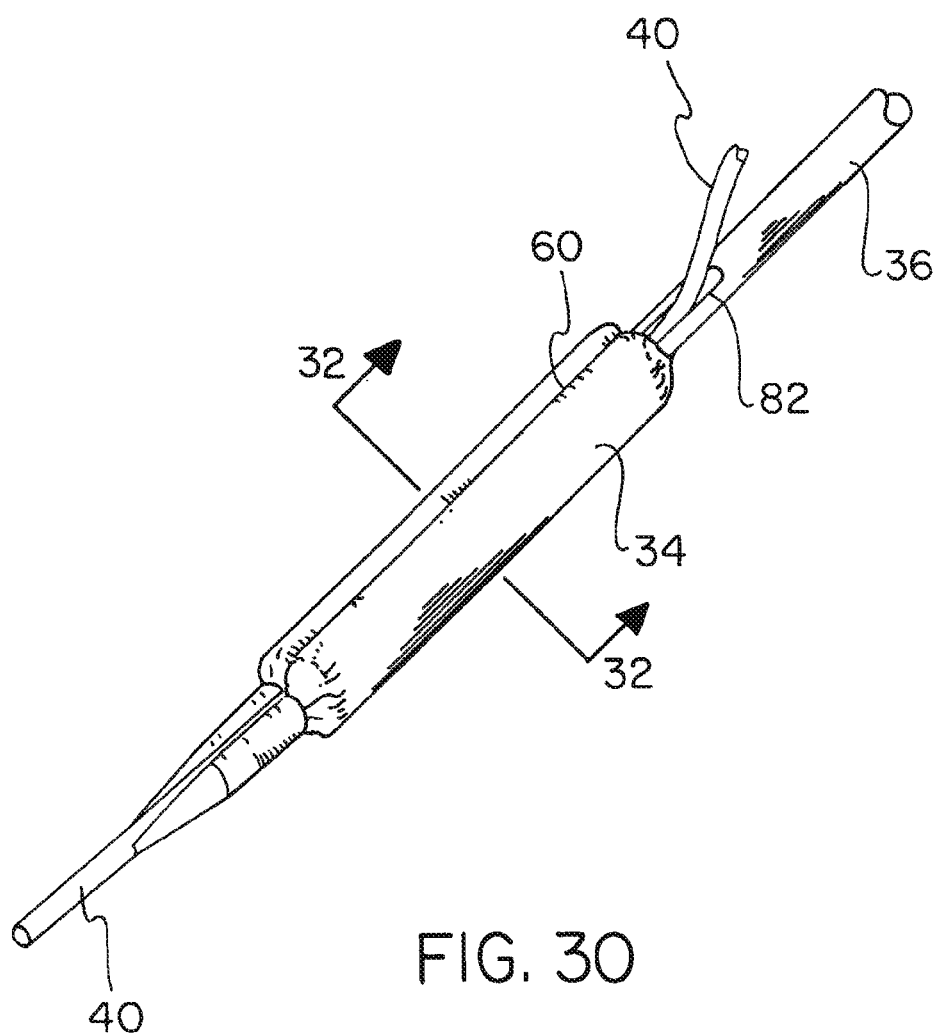
FIG. 30 is an isometric view of another embodiment of the present invention comprising a further example of a disruptable channel formed from the external surface of the balloon itself, having a guidewire retainer within the balloon, and employing a catheter tip with a guidewire centering groove.

Once the deployment apparatus 76 is properly positioned in the branch vessel 48, a second stent 78 can then be deployed, as is shown in FIG. 28. Since the first balloon 34 did not have to be removed to allow introduction of the second deployment apparatus 76, the physician then has the option of immediately reinflating the first balloon 34, as is shown in FIG. 29, in order to make sure both stents 44, 78 are fully and properly deployed in the two vessels 46, 48. The ability to perform simultaneous ballooning of both of these stents using a single guidewire is believed to be particularly unique to the present invention. This allows this procedure to be completed faster and more efficiently than in any previously available stent deployment method.

Still further embodiments of the present invention are illustrated in FIGS. 30 through 47.

Figure 31:
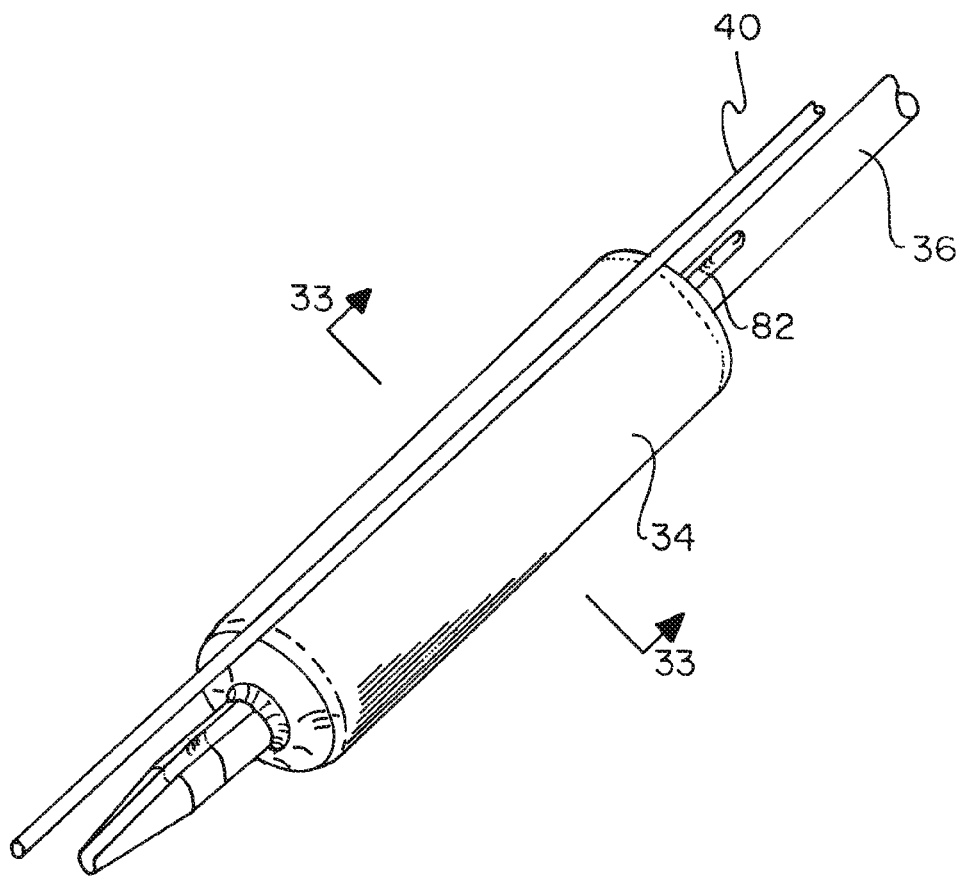
FIG. 31 is an isometric view of the embodiment of FIG. 18, showing the balloon fully inflated, releasing the guidewire from the channel formed in the balloon, and the guidewire separated from the centering groove in the catheter tip.
Figure 32:
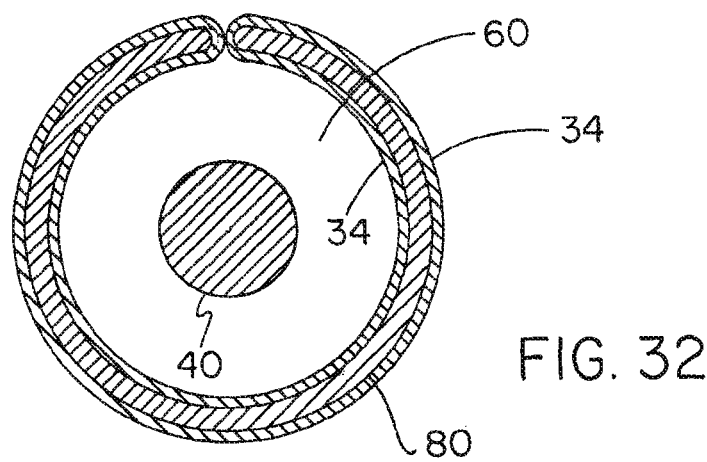
FIG. 32 is a cross section view along line 32-32 of FIG. 30.
Figure 33:
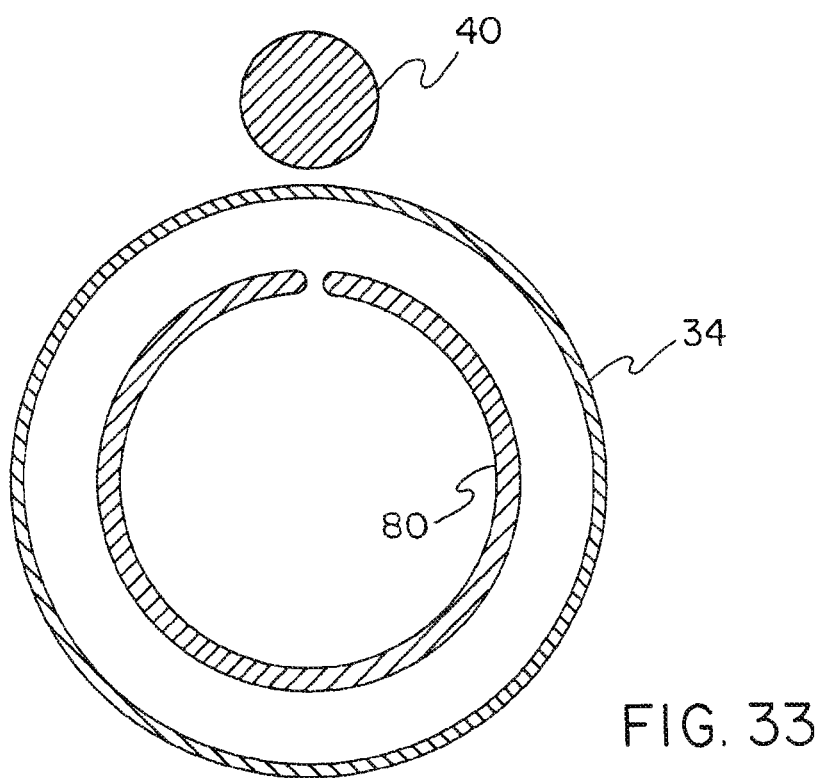
FIG. 33 is a cross section view along line 33-33 of FIG. 31.

FIGS. 30 through 34 illustrate an embodiment of the present invention that improves on the embodiment illustrated in FIGS. 18 and 19. As was previously described, a disruptable guidewire channel 60 can be formed from the external surface of the balloon 34 itself. In this embodiment, a flexible guidewire retainer 80 is contained within the balloon 34 to aid in holding the guidewire 40 within the guidewire channel 60. When the balloon 34 is inflated, as is shown in FIGS. 31 and 33, the balloon 34 applies an outward force that causes the guidewire retainer 80 to flex open releasing the portion of the balloon contained within the guidewire retainer, therefore releasing the guidewire 40. The centering groove in the tip could be a continuation of the guidewire retainer inside the balloon or attached thereto. The guidewire retainer inside the balloon could be a continuation of the support member or attached thereto. The guidewire retainer could also be a continuation of the inflation lumen or attached thereto. The support member could be integral to the guidewire retainer. An indentation 82 can be formed in the catheter shaft 36 to assist in the transition of the guidewire into the guidewire channel 60.

Figure 34:
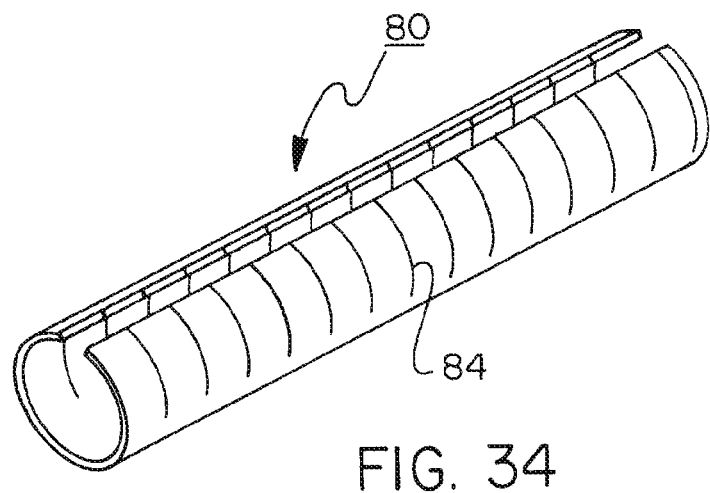
FIG. 34 is an isometric view of one embodiment of a guidewire retainer for use in the embodiments of FIGS. 30 through 33.

One embodiment of a guidewire retainer 80 is shown in FIG. 34. The guidewire retainer 80 comprises a cylinder with at least a semi-circular cross section.

Figure 35:
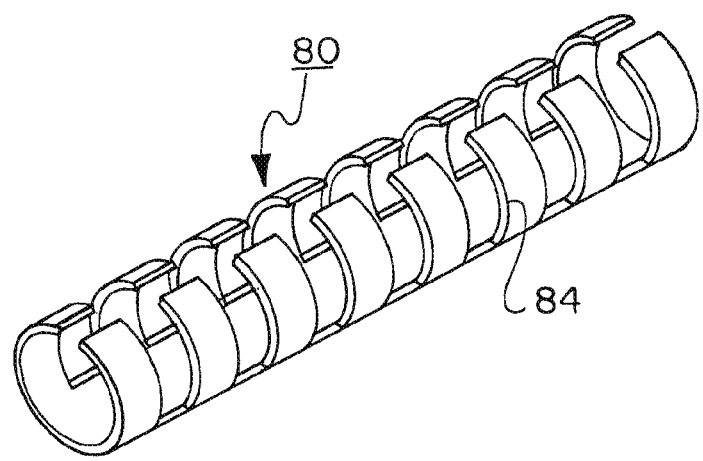
FIG. 35 is an isometric view of another embodiment of a guidewire retainer for use in the embodiments of FIGS. 30 through 33.
Figure 36:
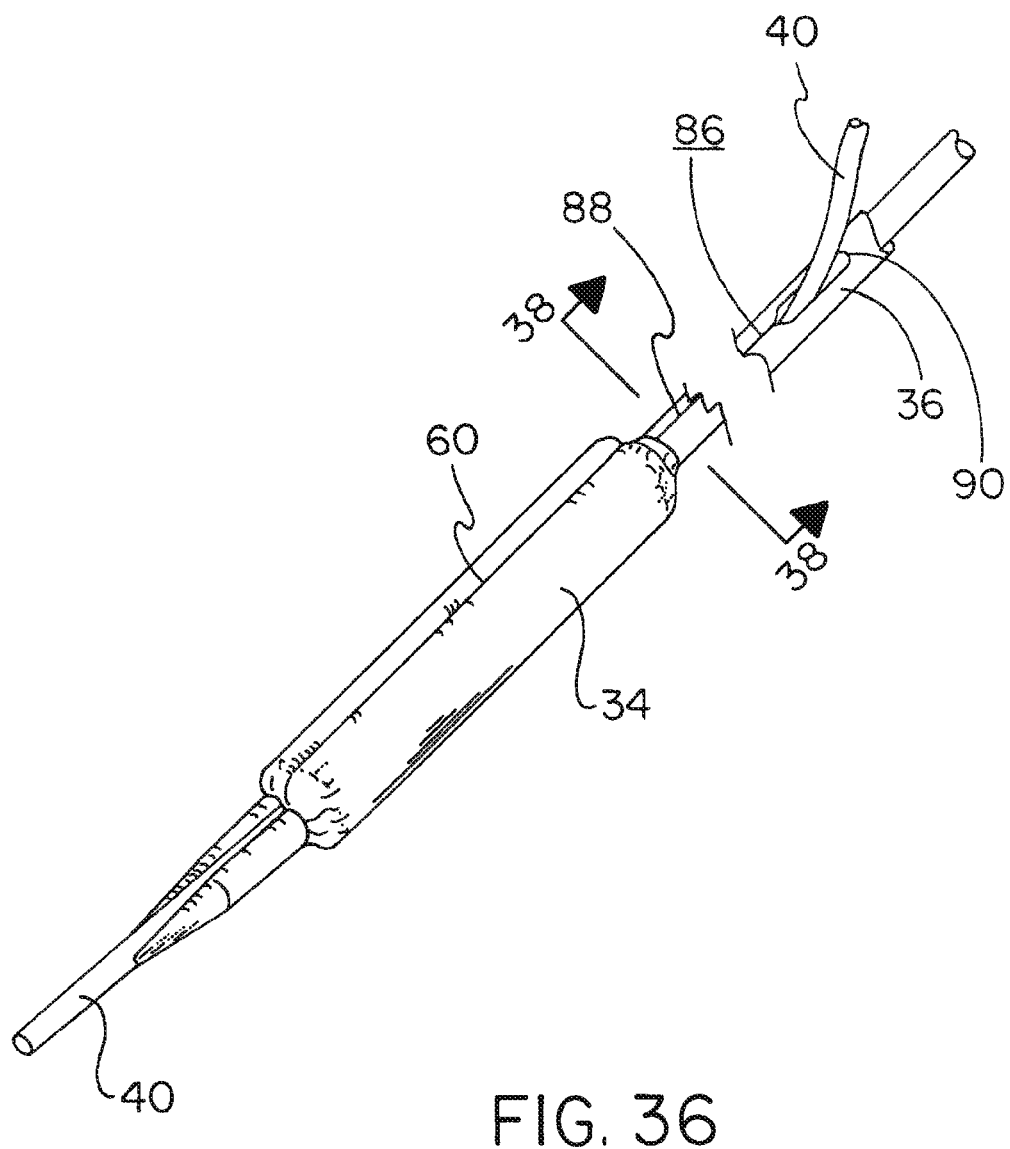
FIG. 36 is an isometric view of still another embodiment of the present invention comprising another example of a disruptable channel formed in the balloon itself, having a guidewire retainer placed within the balloon, employing a catheter tip with a guidewire centering groove, and employing a disruptable channel in the catheter tube proximal to the balloon.

The retainer may comprise any form that provides some gripping of the guidewire, including a tube having a longitudinal slice down its length to the more longitudinally slotted constructions of FIGS. 34 and 35. One or more slits 84 can be provided in the retainer 80 to aid in its flexibility and adjust the pressure necessary to release the guidewire and a portion of the balloon from the retainer. The guidewire retainer 80 can be constructed from any suitably flexible and resilient material, including various plastics or metals. FIG. 35 illustrates that the width of the slits 84 in the guidewire retainer 80 can be altered to aid in its flexibility, adjust the release properties of the retainer relative to the particular materials used to create the retainer, as well as adjust the operating parameters of the balloon. It should be evident from this description that the shape, form, materials, and number of the guidewire retainer(s) 80 used in any given application of the present invention may take a wide variety of forms.

Figure 37:
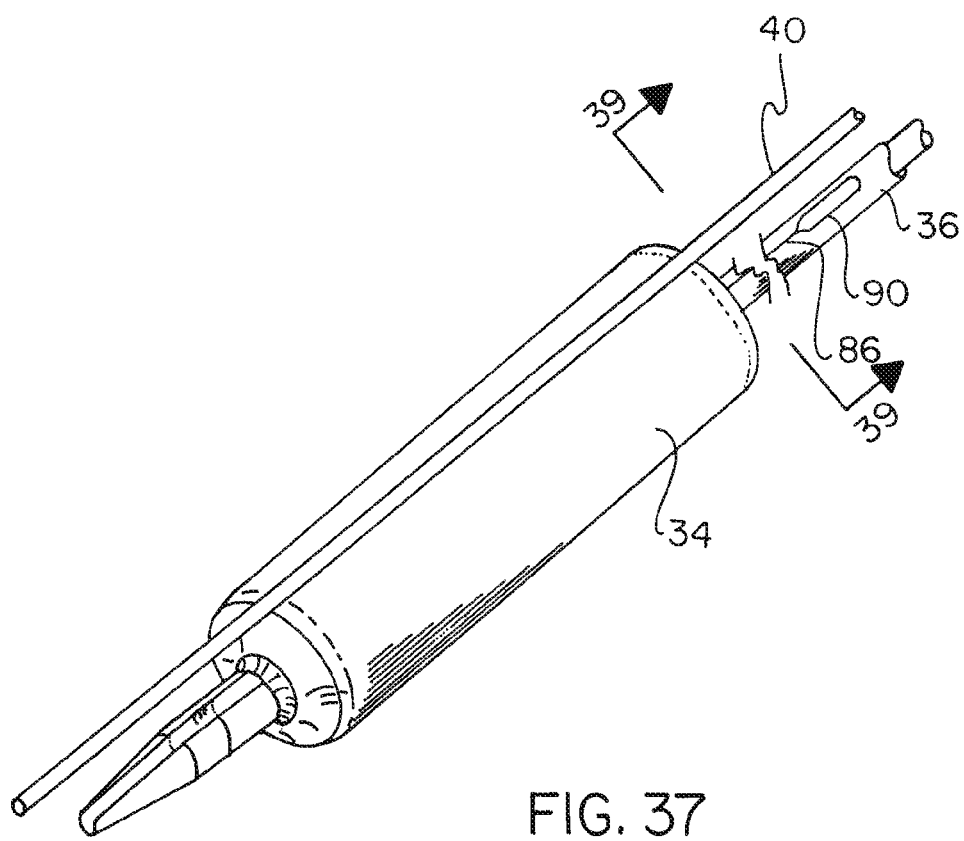
FIG. 37 is an isometric view of the embodiment of FIG. 18, showing the balloon fully inflated, releasing the guidewire from each of the balloon, the centering groove in the catheter tip, and the disruptable channel in the catheter tube.
Figure 38:
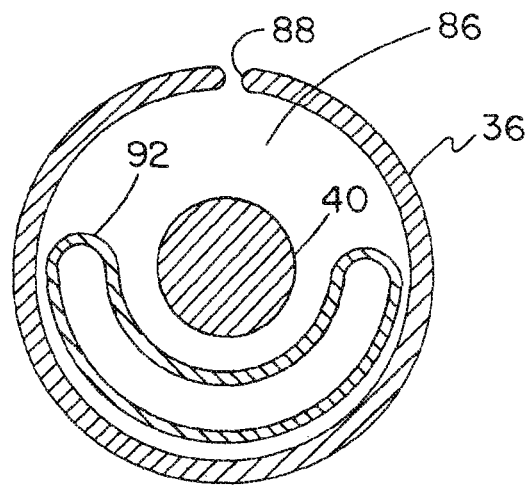
FIG. 38 is a cross section view along line 38-38 of FIG. 36.
Figure 39:
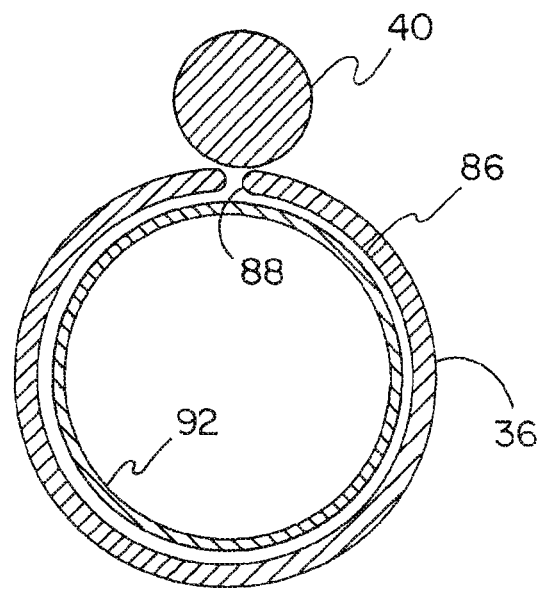
FIG. 39 is a cross section view along line 39-39 of FIG. 37.

This embodiment of the present invention may be further improved by providing releasable retention means in the catheter proximal to the balloon, as is illustrated in FIGS. 36 through 39. As is shown, a channel 86 is provided in the catheter 36 proximal to the balloon 34 that is disruptable. The channel comprises a longitudinal slit 88 in the catheter shaft and an guidewire port 90. This proximal attachment of the guidewire 40 may be beneficial in tracking the balloon into place in the body. The channel 86 may be any suitable length, including a length of less than 5 cm to 25 cm or more from the balloon. When the balloon is inflated, as is shown in FIG. 37, the guidewire 40 will actuate out of the disruptable channel 86 to become completely free from the balloon 34 and catheter 36. In certain applications (e.g., when a longer disruptable channels 86 is employed), it may be desirable to include a collapsible inflation lumen 92, as shown in FIG. 38 that will inflate when pressure is applied to the balloon. As is shown in FIG. 39, when the collapsible lumen 92 is inflated, the collapsible lumen 92 will fill the catheter shaft 36 to force the guidewire 40 out of the channel 86.

Figure 40:
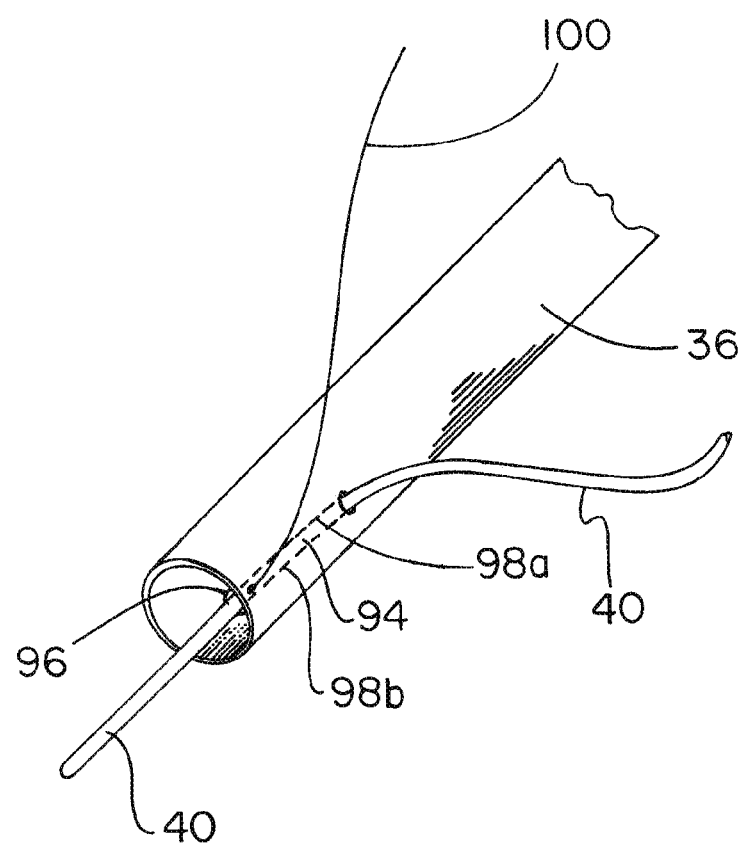
FIG. 40 is an isometric view of a further embodiment of a catheter including a disruptable channel of the present invention.
Figure 41:
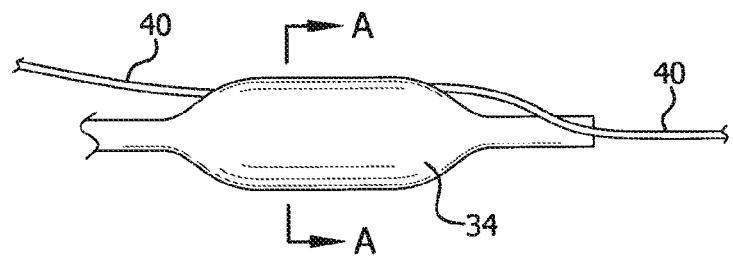
FIG. 41 is a side view of yet another guidewire channel of the present invention wherein the guidewire channel is formed in the wall of the balloon.

FIG. 40 illustrates another embodiment of the present invention wherein the catheter shaft 36 includes a peelable sheath 94 covering the guidewire channel 96. The sheath 94 is disruptably attached to the catheter shaft 36, such as through use of perforation lines 98a, 98b. An actuation cord 100 is attached to one end of the sheath 94. In this embodiment the guidewire channel 96 can be disrupted at any desired time simply by pulling on the actuation cord 100 to remove the sheath 94 and free the guidewire 40.

Figure 42:
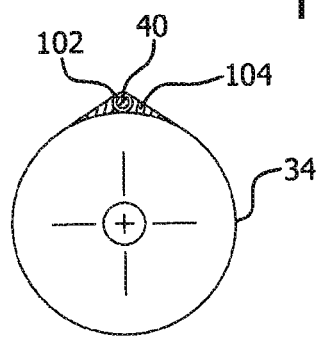
FIG. 42 is a cross section view along line A-A of FIG. 41 showing one embodiment of a guidewire channel that can be formed in the wall of the balloon.
Figure 43:
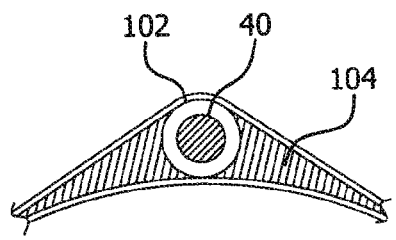
FIG. 43 is an enlarged sectional view of the guidewire channel of FIG. 42.
Figure 44:
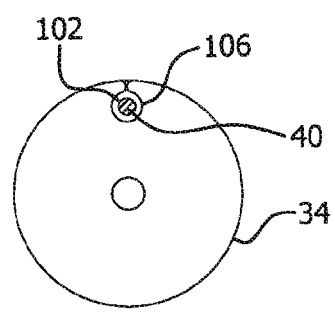
FIG. 44 is a cross section view along line A-A of FIG. 41 showing another embodiment of a guidewire channel that can be formed in the wall of the balloon.
Figure 45:
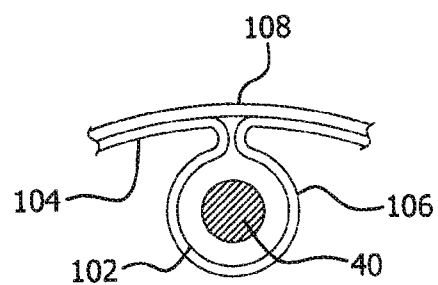
FIG. 45 is an enlarged sectional view of the guidewire channel of FIG. 44.
Figure 46:
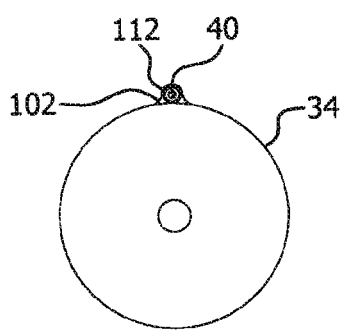
FIG. 46 is a cross section view along line A-A of FIG. 41 showing still another embodiment of a guidewire channel that can be formed in the wall of the balloon.
Figure 47:
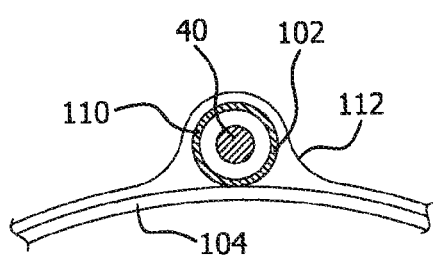
FIG. 47 is an enlarged sectional view of the guidewire channel of FIG. 46.

Other versions of the present invention are shown in FIGS. 41 through 47. In these embodiments, a guidewire channel 102 is formed in the wall 104 of the balloon 34. As is shown in FIGS. 42 and 43, the guidewire channel 102 may be integral with the balloon itself, with the lamina of the balloon wall 104 fully surrounding the channel 102. FIGS. 44 and 45 demonstrate that the guidewire channel 102 may alternatively comprise in invagination 106 formed into the balloon wall. The invagination 106 may include a cover 108 to assist in maintaining the guidewire 40 within the channel 102. FIGS. 46 and 47 illustrate that the guidewire channel 102 may comprise a separate component 110 that is attached to the balloon 34, such as through use of an adhesive or a cover 112. One skilled in the art will appreciate that similar constructs can be achieve through other means including direct extrusion of the balloon material. Likewise, one skilled in the art will further appreciate that one or more such channels 102 may be provided in any given balloon and/or a single relatively wide channel can be provided in the balloon to allow passage of multiple guidewires.

In a further aspect of the invention, either or both of the catheter assembly and the guidewire can be a balloon-on-wire device comprising a longitudinally extending wire having a length, an outer surface, a proximal end, a distal end, and an expandable balloon having an interior space, the balloon being located at the distal end of the wire. In a further aspect of the invention the longitudinally extending wire comprises a lumen defined by an inner surface of the wire and extending from the proximal end of the wire to the distal end and being in communication with the interior space of the balloon. Inflation fluid can be delivered to the interior space of the balloon via the lumen. Moreover, the outer surface of the wire can further comprise at least one cut therein. In a further aspect of the invention the longitudinally extending wire is provided with polymer film covering at least a portion of the outer and/or inner surface thereof. The device further includes a disruptable guidewire channel, as discussed in detail above.

The longitudinally extending wire can be any suitable material such as metal or polymer and includes, for example, tubular structures such as polymer tubes, metal tubes (e.g., hypotubes), stranded wires, braided wires, etc.

In yet a further aspect of the invention, the at least one cut in the outer surface of the wire can extend from the outer surface to the inner surface. The at least one cut may be a spirally extending cut extending for any desirable length of the wire. In an aspect of the invention, the spirally extending cut can extend from the proximal end to the distal end of the wire. Moreover, the pitch of the spiral cut can be varied from one point to a second point along the length of the wire to vary the flexibility of the wire over a desired length of the wire.

In an aspect of the invention, the polymer film can be provided as a polymer film wrap. In a further aspect of the invention, the polymer film can be provided as a tubular shrink wrap. With regard to the polymer film wrap, in an aspect of the invention, the polymer film wrap is provided as a helical wrap. Moreover, in an aspect of the invention, the polymer film wrap comprises porous expanded polytetrafluoroethylene ("ePTFE"). Exemplary films and methods of film wrapping are disclosed in commonly owned and copening U.S. Patent Application Publication Number 2005/0059957, the subject matter of which is herein incorporated by reference.

Suitable polymer films include, for example, flexible polymer materials such as polyethylene, including ultra-high molecular weight polyethylene, polypropylene, polyamide, polyethylene terephthalate, fluorinated ethylene propylene (FEP), perfluoro alkoxy resin (PFA), polyurethane, polyester, polyimide, etc. Porous polymers, optionally provided with a thin, non-porous coating, may be advantageously used because of their excellent flexibility. The polymer film is most preferably made from a thin, ePTFE film that has been provided with a porous or non-porous coating of a thermoplastic such as a thermoplastic fluoropolymer, preferably fluorinated ethylene propylene (FEP). EPTFE films can be made as taught by U.S. Pat. Nos. 3,953,566 and 4,187,390 to Gore and U.S. Pat. No. 5,476,589 to Bacino. It may be desirable to modify the polymer film material by providing various fillers to the film. In the case of porous polymers such as ePTFE film, fillers can be imbibed into the porosity of the film by known methods, such as taught by U.S. Pat. No. 5,879,794, to Korleski. Suitable fillers include, for example, fillers in particulate and/or fiber form and can be ceramics, metals, metalloids, carbon, and combinations thereof. Particularly useful fillers include, for example, radiopaque materials, such as, for example, gold, barium sulfate, bismuth subcarbonate, tungsten, and tantalum. The fillers can be used in combination with desired adhesive materials when imbibed into the porosity of the polymer film. It may also be desirable to metalize the film on at least a portion thereof. Moreover, ePTFE/FEP laminate films are taught in U.S. Pat. No. 6,159,565, to Campbell et al. In an aspect of the invention, the polymer film is provided in a helically-wrapped fashion. In a further aspect of the invention, polymer films which exhibit longitudinal shrinkage (e.g., by heat or chemical activation) may be particularly attractive for use in certain aspects of the invention. Further suitable polymer films can be polymer tubes which may be heat shrinkable materials. One such material is PET shrink tubing, which can be provided in very thin (e.g., 0.5 mil) thicknesses. ePTFE is another example of polymer film (or tubing) that may exhibit shrinkage upon either chemical or heat activation.

It may be desirable to provide a suitable adhesive material to at least a portion of at least one side of the polymer film. Any number of adhesives may be useful according to this aspect of the invention; including thermoplastic adhesives, thermoset adhesives, pressure sensitive adhesives, heat activated adhesives, chemically activated adhesives, and UV-curable adhesives, depending upon the particular embodiment and desired results. The adhesives can be provided in liquid or solid form. In an aspect of the invention, adhesives include, for example, polyamides, polyacrylamides, polyesters, polyolefins (e.g., polyethylene), polyurethanes, and the like.

With regard to film wrapping of cut wire, it is believed that an ePTFE/adhesive laminate film may be particularly useful.

For example, it may be desirable to provide an adhesive to the outer surface, the inner surface, or both, of the ePTFE film to provide for enhanced properties. In such a case, it is believed that the ePTFE is particularly attractive, since the ePTFE may act as a stable scaffold (i.e., the film tends to shrink only a small amount) for the adhesive. For example, when wrapping a metal hypotube with an ePTFE/FEP system, the FEP could act as an adhesive, the system could be heated to cause the FEP to flow; however, the FEP will tend to stay in the ePTFE structure and not infiltrate into the fenestrations in the hypotube. Further embodiments could include wrapping a cut PEBAX tube with an ePTFE film and an adhesive with a lower melting temperature—or indeed a UV curable adhesive.

Figure 48:
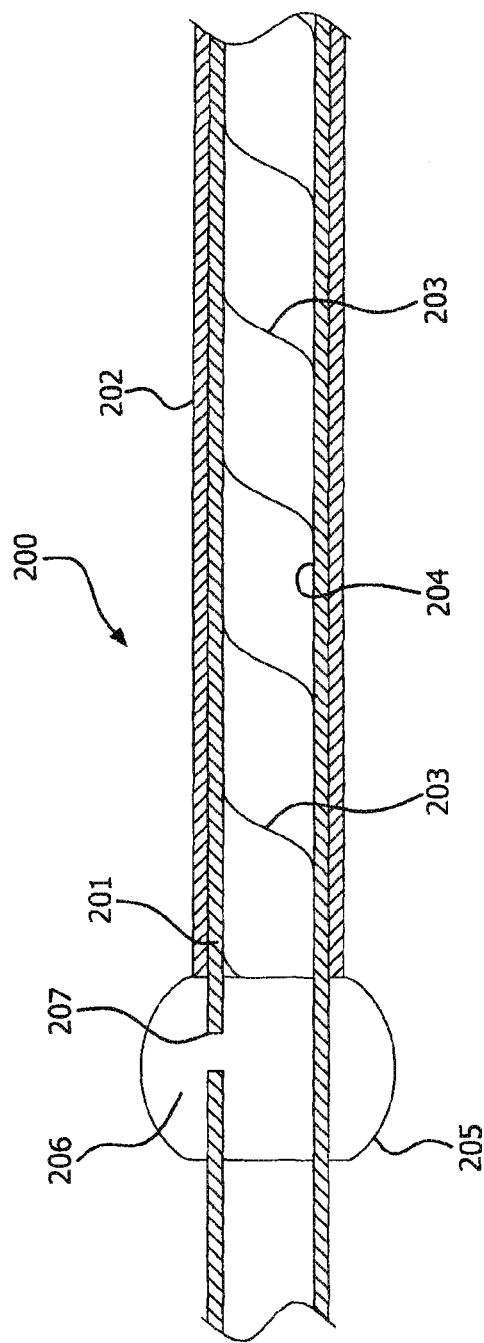
FIG. 48 is a longitudinal cross-section of a balloon-on-a-wire device according to an aspect of the invention.

FIG. 48 is a longitudinal cross-sectional view of an exemplary balloon-on-a-wire device of the present invention comprising a spiral cut wire 201 (e.g., a metal tube such as hypotube) wrapped with a film layer 202. The cuts 203 in the wire 201 are essentially sealed by the film wrap 202. The desired flexibility of the wire 201 is maintained and by the addition of the film wrap 202, a sealed fluid lumen 204 is formed within the wire. Near the distal end of the device 200 is expandable balloon 205 having an interior 206. The balloon interior 206 is in communication with lumen 204 via port 207. The device will further include a disruptable guidewire channel (not shown), as discussed above. Moreover, the wire 201 can be provided with a spiral cut with changing pitch across all, or a part of, the length of the wire, thus providing a flexibility transition region in the wire. Of course, desirable flexible wire can be obtained by other means than providing a spiral cut wire. In this regard any longitudinally extending wire having at least one cut in its outer surface or through its wall may be used. Any desirable number of cuts can be provided. For example, strategically placed cuts could be located at any number of locations along the length and/or around the circumference of the wire. The cuts in the wire could be strategically arranged to provide for varying flexibility across the length of the wire.

In a further aspect of the invention, a stent or stent-graft (not shown) can be mounted over the expandable balloon 205.

It is also possible to provide at least one radiopaque material to the device. The radiopaque material can be any suitable material and can be located at any desired point along the length of the device.

The device may further comprise a stiffening device, which may be located in the at least one lumen. In an aspect of the invention, the stiffening device is capable of being moved proximally and distally in the at least one lumen. Suitable stiffening devices include, for example, stylets, wires, tubes, braids, and combinations thereof. The stiffening device may be solid or hollow. Moreover, the stiffening device can have a variable stiffness along at least a portion of its length. Further, the stiffening device may comprise any suitable material, such as, metal, metalloids, and polymers.

It should be noted that the inner surface or the outer surface of the wire can be pretreated (i.e., chemically etched, etc.) prior to providing the polymer film or covering to the surface.

With respect to virtually all of the embodiments of the present invention, an additional benefit may be realized by the fact that the guidewire is positioned on the outside of the balloon. It is theorized that it can be beneficial under certain circumstances not to evenly balloon a plaque occlusion in a blood vessel. By applying a focused force at distinct areas around the circumference of the vessel during ballooning, it is believed that the plaque may more successfully be disrupted. Where focusing of expansion forces is desired, the presence of the guidewire on the outside of the balloon may provide a ready means to accomplish improved plaque treatment. In such instances it may be desirable to provide radiopaque markers on the guidewire channel to aid in positioning the balloon and guidewire and effectuating focused ballooning.

Without intending to limit the scope of the present invention, the following example illustrates how the present invention may be made and used.

EXAMPLE

One embodiment of the present invention can be constructed by modifying a commercially available balloon catheter device.

A 4.0 mm×30 mm RX GEMINI Coronary Balloon Dilatation Catheter available from Guidant/ACS of Santa Clara, Calif., may be used as the starting catheter device and is modified in the following manner:

1. Insert a 0.36 mm diameter stainless steel wire in the tip and advance it proximally until it exits the RX port.
2. Measure the distance from the tip to RX port.
3. Remove and cut the 0.36 mm wire to the measured length.
4. Reinsert the 0.36 mm wire. Use the EFD dispensing tip to wick Loctite 4014 into the proximal RX channel and at the distal tip to secure the 0.36 mm wire.
5. A sleeve of the present invention is cut from a film or tube of expanded PTFE having the following dimensions: not longer than the balloon, but long enough to provide optimal trackability; the width should be at least as wide as the diameter of the guidewire and sufficient to attach across enough of the balloon so that the sleeve will disrupt when the balloon is inflated.
6. Perforations are formed in the sleeve by holes 0.64 mm in diameter on 1.02 mm centers along the entire length of the sleeve cutting using a $CO_2$ laser.
7. The sleeve is permanently attached to the Guidant/ACS balloon by any suitable fashion, preferably adhesive such as Loctite 4014 cyanoacrylate.
8. Apply a bead of adhesive along the length of the balloon.
9. Place one side of the sleeve lengthwise onto the bead of adhesive, securing the sleeve to the balloon, ensuring that the other side of the sleeve is free.
10. Place an appropriate sized mandrel for the proper guidewire size along the balloon and under the sleeve flap.
11. Apply a bead of adhesive onto the balloon at an appropriate location to secure the free end of the sleeve. Wrap the sleeve over the mandrel and onto the adhesive bead, securing the sleeve to the balloon and creating a space to accommodate a future guidewire.

A balloon catheter device of the present invention is created through this above described process. The catheter includes a guidewire channel attached to the exterior of the balloon that is disruptable upon inflation of the balloon so as to free the guidewire from the guidewire channel.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. An expandable balloon and catheter assembly comprising:
   a catheter shaft having a length;
   an expandable catheter balloon having an exterior surface, said expandable catheter balloon being mounted on the catheter shaft;

a sleeve attached to a portion of the exterior surface of the expandable catheter balloon forming a guidewire channel along at least a portion of the balloon;

a balloon-on-a-wire device comprising an elongated wire having a length, an outer surface with at least one spirally extending cut therein, an inner surface defining a longitudinally extending lumen, a proximal end, and a distal end, an expandable balloon having an interior and being located at the distal end of the wire, with the interior being in fluid communication with the longitudinally extending lumen, and polymer film covering at least a portion of the outer surface of the wire, the balloon-on-a-wire device at least partially placed within the sleeve;

wherein the sleeve includes a separation line and the sleeve is disruptable by parting along the separation line when the expandable catheter balloon is expanded, separating and releasing the balloon-on-a-wire device from the expandable catheter balloon; and wherein the separation line comprises an attachment line between the expandable catheter balloon and the sleeve.

2. The assembly of claim 1, wherein the separation line comprises a line of perforations formed in the sleeve.

3. The assembly of claim 1, wherein the polymer film is a polymer film wrap.

4. The assembly of claim 3, wherein the polymer film comprises ePTFE.

5. The assembly of claim 1, wherein the polymer film is a tubular shrink wrap.

6. The assembly of claim 4, wherein the polymer film is a helical wrap.

7. The assembly of claim 6, wherein the wire comprises a hypo-tube.

* * * * *